United States Patent
Phillips et al.

(10) Patent No.: US 10,220,126 B2
(45) Date of Patent: Mar. 5, 2019

(54) BREAST SHIELD AND BREAST PUMP DEVICE

(71) Applicant: P.H.D. Devices, LLC, Salt Lake City, UT (US)

(72) Inventors: Andrew Luke Phillips, Salt Lake City, UT (US); Eugene Jason Huo, Salt Lake City, UT (US); Christopher Catlett Duncan, Salt Lake City, UT (US)

(73) Assignee: P.H.D. DEVICES, LLC, Salt Lake City, UT (US)

( * ) Notice: Subject to any disclaimer, the term of this patent is extended or adjusted under 35 U.S.C. 154(b) by 295 days.

(21) Appl. No.: 15/094,913

(22) Filed: Apr. 8, 2016

(65) Prior Publication Data

US 2016/0296682 A1 Oct. 13, 2016

Related U.S. Application Data

(60) Provisional application No. 62/144,713, filed on Apr. 8, 2015.

(51) Int. Cl.
*A61M 1/06* (2006.01)
*A61J 13/00* (2006.01)

(52) U.S. Cl.
CPC .............. *A61M 1/062* (2014.02); *A61J 13/00* (2013.01); *A61M 1/066* (2014.02);
(Continued)

(58) Field of Classification Search
CPC .......... A61J 13/00; A61M 1/06; A61M 1/062; A61M 1/064
See application file for complete search history.

(56) References Cited

U.S. PATENT DOCUMENTS

| 22,018 A | 11/1858 | Davidson |
| 420,195 A | 1/1890 | Graves |

(Continued)

FOREIGN PATENT DOCUMENTS

| WO | 2008057218 A2 | 5/2008 |
| WO | 2008137678 A1 | 11/2008 |

(Continued)

OTHER PUBLICATIONS

"Freemie—Pump Hands-Free," <http://www.freemie.com/index.html>, retrieved Apr. 6, 2016.

(Continued)

*Primary Examiner* — Nathan R Price
*Assistant Examiner* — Courtney Fredrickson
(74) *Attorney, Agent, or Firm* — Banner & Witcoff, Ltd.

(57) ABSTRACT

A breast pump device for pumping breast milk is disclosed. The breast pump device may include a breast shield for receiving a breast, a collection container for receiving breast milk, a tubing connecting the breast shield to the collection container, and a pump connected to the collection container, configured to draw breast milk from the breast shield, through the tubing, and into the collection container. The breast shield may include a channel extending from an interior portion of the breast shield located near a nipple of the breast to an exterior portion of the breast shield. The various components of the breast pump device may be made out of antimicrobial materials. One or more sensors and/or computing devices may be incorporated to measure the amount of milk produced, monitor temperature of the milk, and provide alerts regarding pumping schedules.

20 Claims, 28 Drawing Sheets

(52) U.S. Cl.
CPC . *A61M 2205/18* (2013.01); *A61M 2205/3331* (2013.01); *A61M 2205/3334* (2013.01); *A61M 2205/3368* (2013.01); *A61M 2205/3379* (2013.01); *A61M 2205/3553* (2013.01); *A61M 2205/3584* (2013.01); *A61M 2205/3592* (2013.01); *A61M 2205/502* (2013.01)

(56) References Cited

U.S. PATENT DOCUMENTS

| | | | | |
|---|---|---|---|---|
| 3,667,463 | A * | 6/1972 | Barnes | A61M 16/16 128/203.16 |
| 4,270,538 | A | 6/1981 | Murphy | |
| 6,379,327 | B2 | 4/2002 | Lundy | |
| 6,440,100 | B1 | 8/2002 | Prentiss | |
| 7,223,255 | B2 | 5/2007 | Myers et al. | |
| 8,945,046 | B2 * | 2/2015 | Brittner | A61M 1/06 604/73 |
| 2008/0039781 | A1 | 2/2008 | Bjorge | |
| 2008/0045888 | A1 * | 2/2008 | Edwards | A61J 11/0005 604/76 |
| 2008/0262420 | A1 | 10/2008 | Dao et al. | |
| 2010/0179472 | A1 * | 7/2010 | Weston | A61M 1/06 604/67 |
| 2011/0071466 | A1 * | 3/2011 | Silver | A61M 1/06 604/74 |
| 2013/0023821 | A1 * | 1/2013 | Khalil | A61M 1/06 604/74 |

FOREIGN PATENT DOCUMENTS

| | | |
|---|---|---|
| WO | 2011035448 A1 | 3/2011 |
| WO | 2011037841 A2 | 3/2011 |

OTHER PUBLICATIONS

"Babyation," <http://www.babyation.com>, retrieved Apr. 6, 2016.
"Freemie Collection Cups," User Manual, dated Mar. 17, 2015.
"Freemie Equality Pump Set," User Manual, dated Mar. 19, 2015.
"Freemie Freedom Pump Set," User Manual, dated Mar. 19, 2015.
"Freemie Breast Pump Collection System," Quick Set-up Guide, dated Mar. 23, 2015.

* cited by examiner

BREAST SHIELD AND BREAST PUMP DEVICE

CROSS-REFERENCE TO RELATED APPLICATION

This application claims the benefit of U.S. Provisional Application No. 62/144,713, filed Apr. 8, 2015, which is incorporated by reference in its entirety.

BACKGROUND

Feeding infants exclusively breast milk is recommended for the first six months of life. But in the United States, less than twenty percent of mothers are meeting this recommendation due, at least in part, to inconvenience of breast feeding. Although breast pump devices exist, these devices also carry inconveniences. For example, many breast pump devices are bulky, require a private room for a mother to undress and secure the device, and they are difficult to clean. Thus, there is a need for an improved breast pump.

SUMMARY

The following summary is for illustrative purposes only, and is not intended to limit or constrain the detailed description.

Aspects of the disclosure provide effective, efficient, scalable, and convenient technical solutions that address and overcome the technical problems associated with breast pump devices. Specifically, aspects of the disclosure relate to breast pump devices that can pump milk underneath a woman's normal clothing, allow for hands-free pumping, and are faster and more convenient to clean.

In accordance with one or more embodiments, a breast pump device may include one or more of a breast pump shield, a collection container, a pump, and tubing. In some embodiments, a breast pump shield may include a curved convex exterior portion, a concave interior portion configured to receive and support a human breast, the concave interior portion, when placed against the breast, forming a seal. In some embodiments, the breast pump shield may include a chamber connected to the concave interior portion, the chamber configured to receive a nipple of the breast. In some embodiments, the breast pump shield may include a reservoir connected to an end of the chamber opposite an end of the chamber connected to a concave surface of the concave interior portion, and a channel connected to the reservoir, the channel configured to receive a tubing.

In some embodiments, the tubing may include a collection tubing that connects the breast shield to a collection container. In some embodiments, when a pump is connected to the collection container, the pump may be configured to draw milk from the breast, through the chamber, through the reservoir, through the channel, through the collection tubing, into the collection container.

In some embodiments, the breast shield may include a ring disposed within the chamber, between the reservoir and the concave interior portion, the nipple of the breast contacting the ring when suction is applied to the nipple via the breast shield. In some embodiments, a thickness of the breast shield may be less than a diameter of the breast shield, such that the breast shield has a low profile.

In accordance with one or more embodiments, a breast pump device may include a breast shield for receiving a human breast, a collection container for receiving breast milk, a collection tubing connecting the breast shield to the collection container, a pump tubing connecting the pump to the collection container, and a pump connected to the collection container via the pump tubing, the pump configured to draw breast milk from the breast via the breast shield, through the tubing, and into the collection container.

In some embodiments, the collection tubing may be connected to a side portion of the breast shield. In some embodiments, the collection tubing may be connected to an inferior portion of the breast shield at or near a midline of the breast shield. In some embodiments, the breast pump device may include a connector connecting the collection tubing with the side portion of the breast shield, the connector being configured to receive any of a plurality of collection tubings of different respective diameters.

In some embodiments, the pump tubing connecting the pump to the collection container may be shorter than the collection tubing connecting the breast shield to the collection container. In some embodiments, the collection tubing may be at least twelve inches long. In some embodiments, the collection container, when the breast shield is attached to the breast, may be outside of a shirt of a user of the breast shield. In some embodiments, the breast shield may be attached to the breast by a process that may be performed without a user of the breast shield removing a shirt of the user.

In some embodiments, the breast shield may be made of a flexible material, such as silicone. In some embodiments, a longest length of a portion of the breast shield that contacts an area around the breast may be less than four times a thickness of the breast shield.

In some embodiments, the breast shield may include a channel extending from a reservoir of the breast shield located near a nipple of the breast to a side of an exterior portion of the breast shield, and a breast shield tubing extending along the channel, an end of the breast shield tubing connecting to the collection tubing connecting the breast shield to the collection container.

In some embodiments, the breast pump device may include a pressure gauge connected between a first portion of the pump tubing and a second portion of the pump tubing, the pressure gauge being configured to measure a suction created by the pump against the breast.

In accordance with one or more embodiments, a system may include a breast shield configured to be placed on a human breast, a collection container connected to the breast shield via collection tubing, the collection container including a flow-volume sensor. In some embodiments, the system may include a pump connected to the collection container via pump tubing, the pump configured to use suction to draw breast milk from the breast via the breast shield, through the collection tubing to the collection container. In some embodiments, the system may include a computing device with one or more processors and non-transitory memory storing executable instructions that, when executed by the one or more processors, cause the computing device to receive an indication of a pump start time, receive flow volume information from the flow-volume sensor of the collection container for a duration of a pumping session, determine a decrease in flow volume based on the received flow volume information, receive an indication of a pump stop time, and determine, based on the pump start time, the flow volume information, and the pump stop time, a total volume of the breast milk pumped during the pumping session.

In some embodiments, the collection container may be used during the pumping session to receive the breast milk, and the collection container may include a radio-frequency identification (RFID) tag. In some embodiments, the executable instructions may cause the computing device to receive RFID information including an RFID identifier of the collection container used during the pumping session, and/or associate the RFID identifier of the collection container used during the pumping session with the total volume of the breast milk pumped during the pumping session.

In some embodiments, the collection container may include a temperature sensor. In some embodiments, the executable instructions may cause the computing device to receive temperature information from the temperature sensor of the collection container for the duration of the pumping session, determine, based on the temperature information, one or more of a high temperature of the breast milk collected during the pumping session, a low temperature of the breast milk collected during the pumping session, and an average temperature of the breast milk collected during the pumping session, determine whether the one or more of the high temperature, the low temperature, and the average temperature is within an unsafe temperature range, and in a case that the one or more of the high temperature, the low temperature, and the average temperature is within an unsafe temperature range, generate an alert including the RFID information of the collection container used during the pumping session.

The summary here is not an exhaustive listing of the novel features described herein, and is not limiting of the claims. These and other features are described in greater detail below.

BRIEF DESCRIPTION OF THE DRAWINGS

These and other features, aspects, and advantages of the present disclosure will become better understood with regard to the following description, claims, and drawings. The present disclosure is illustrated by way of example, and not limited by, the accompanying drawings in which like numerals indicate similar elements.

DETAILED DESCRIPTION

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure.

Aspects of the disclosure provide effective, efficient, scalable, and convenient technical solutions that address and overcome the technical problems associated with breast pump devices. Specifically, aspects of the disclosure relate to breast pump devices that can pump milk underneath a woman's normal clothing, allow for hands-free pumping, and are faster and more convenient to clean.

Figure 1:
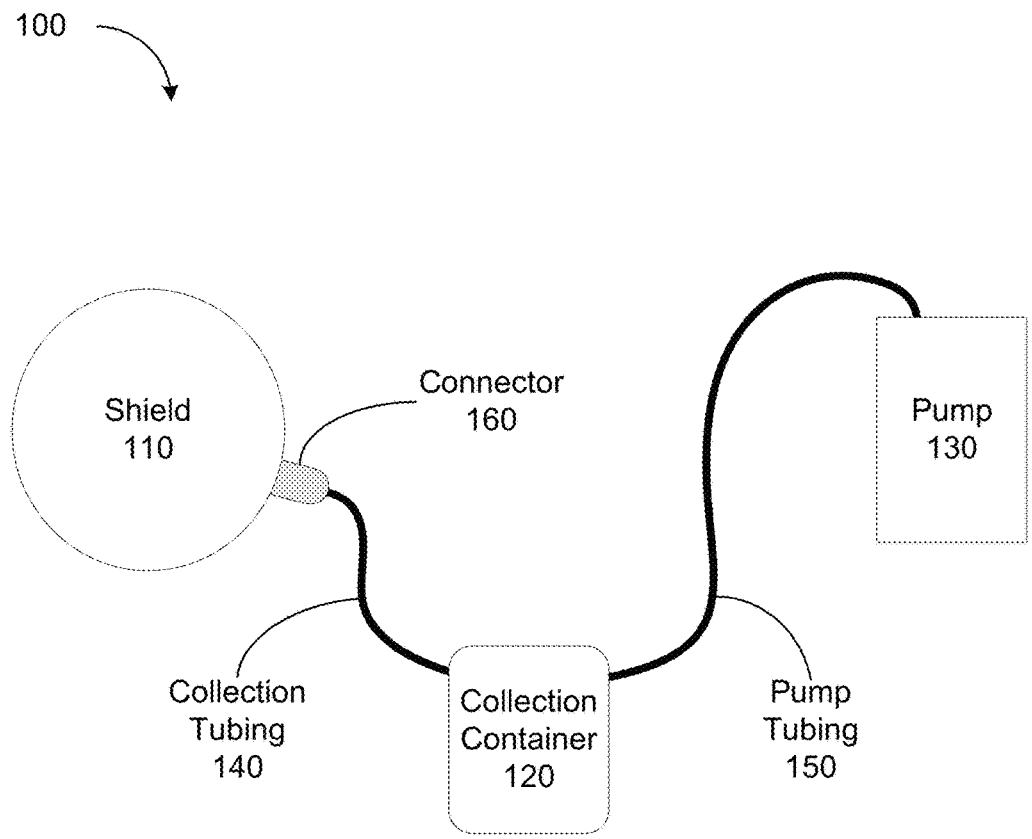
FIG. 1 is an illustrative block drawing of a breast pump device according to at least one embodiment described herein.

A breast pump device may be used for pumping milk from one or both breasts of a mother or a lactating woman. FIG. 1 depicts an illustrative block diagram of one embodiment of a breast pump device (e.g., breast pump device 100). A breast pump device may include one or more breast shields (e.g., breast shield 110), one or more collection containers (e.g., collection container 120), and one or more pumps (e.g., pump 130). One or more pieces of tubing (e.g., collection tubing 140) may connect the breast shield to the collection container. One or more pieces of tubing (e.g., pump tubing 150) may connect the pump with the collection container. In some embodiments, there may be a connector (e.g., connector 160) between the shield and the tubing connecting the shield to the collection container.

The breast pump device may be configured such that when the shield is attached to a breast, milk flows from the nipple through the shield, through the tubing, into the collection container. A mother or lactating woman may operate the system that includes the breast shield, the tubing, the collection container, and the pump until a sufficient quantity of milk is collected in the collection container. The breast pump device allows for hands-free, discreet operation. The breast shield may be worn under a shirt or other clothing of a woman, with the tubing being fed outside of the clothing to a collection container located apart from the breast shield. Thus, the breast shield and breast pump device described herein allows a woman to conveniently and discreetly pump breast milk in any location, without having to partially undress to pump breast milk.

The shield (e.g., shield 110) may be made of a flexible material that can be comfortably worn. For instance, according to at least one embodiment, breast shield 200 may be made of silicone, urethane, polypropylene, or another flexible food-grade material. Breast shield 200 may be made of a silicone-dipped plastic, which may allow for breast shield 200 to hold a vacuum, and/or have a more comfortable interface against the breast. Breast shield 200 may be made of any one or more of the above-mentioned materials, and may be coated in a hydrophobic, food-safe coating (e.g., LiquiGlide), which may permanently create a slippery surface to which milk might not adhere. This may result in easier sanitation, and/or less waste of milk (e.g., most or all of the milk will be pumped through the shield). Some materials (e.g., silicone), when placed against skin, may have a natural grip against the skin, which may assist in creating a seal between the shield and the skin.

In some embodiments, the shield may be made of or contain a material that produces or retains heat. For example, the shield may be warmed before use in a microwave, in warm water, or the like. In some embodiments, the shield may include an electric or chemical warming element. A warm shield may be more comfortable for use. Additionally, there is some evidence that a warm environment may increase milk expression (e.g., an amount of milk produced) and/or blood flow, and therefore a warm shield may result in increased milk production.

In some embodiments, the shield may be a wholly integral unit (e.g., an integrally formed single piece device) that does not require assembly before or after use or cleaning. Illustrative embodiments and further features of a breast shield are discussed in further detail with regard to FIGS. 2-7.

The pump (e.g., pump 130) may be any classification of pump compatible with the breast pump system. For instance, the breast pump may comprise an electric open system, an electric closed system, a battery operated pump, or a manual pump.

In some embodiments, the pump may be connected to the collection container by a pump tubing (e.g., pump tubing 150) such that a vacuum may be applied to the system that includes the pump tubing, the collection container, the tubing, and the breast shield. Alternatively, the pump may be integrated with the collection container.

In some embodiments, a vacuum-sensing device (e.g., a pressure gauge) may be used between the pump and the collection container, and/or between the collection container and the breast shield. The vacuum-sensing device may include a display that shows an amount of pressure being generated within the breast pump device or system by the pump. In some embodiments, the vacuum-sensing device may be integrated into the pump and/or the collection container. The vacuum-sensing device may be used every time that the breast pump device is used, or alternatively may be used occasionally to check the integrity and/or effectiveness of the system. For example, some women experience difficulty when attempting to use a breast pump device (e.g., first-time use may be difficult). In some instances, a breast shield may not be properly sized for a woman (e.g., the breast shield may be too large or too small). If a breast shield is not properly sized, the breast shield might not create a tight seal with the woman's breast, which might not allow the pump system to create sufficient vacuum within the system when the breast pump is in operation. Even if there is some vacuum, the less vacuum there is, the less suction there might be, which may result in less milk production. The vacuum-sensing device may allow a woman to attach the breast shield to her breast, activate the pump, and visually read (e.g., on a display or gauge of the vacuum-sensing device) an amount of vacuum (which may correspond to an amount of suction) being created by the breast pump. If the amount of vacuum is too low, the woman may determine that the breast pump device is not fitting properly, is not functioning properly, or some other issue. Thus, by using a vacuum-sensing device, a user may be able to correctly determine proper system functioning (e.g., by determining a proper shield size), which may allow for optimal seal, vacuum, and suction while using the system, which may result in increased effectiveness (e.g., milk production) when using the breast pump device.

The collection container (e.g., collection container 120) may be a bottle, jar, box, bladder, bag, or other shape. In some embodiments, the collection container may include a hook strap, or other mechanism for attaching the collection container to a belt, bag, purse, or the like. The collection container may be made of a material and/or shape that allows for the collection container to maintain integrity, structure, strength, and/or shape when a vacuum is applied by the pump to the system. For example, the collection container may be made of polypropylene, copolyester, Tritan, or the like.

Having a collection container that, in some embodiments, is separate from both the shield and the pump may provide several benefits. For example, the size of the collection container may be varied (e.g., increased or decreased), which may allow for a desired amount of milk collection, improved portability, and the like. Having the collection container separate from the shield may allow for a lighter shield and/or may allow for the shield to be a consistent weight. For example, if a collection device is integrated with a breast pump device (e.g., collecting milk at or near the breast), a weight of the device may increase through a pumping session as more milk is pumped and the collection device fills with milk.

Additionally, separating the collection container from the rest of the breast pump device allows for increased convenience in pumping milk. For example, in some breast pump systems, a collection container is attached directly to the breast or is closely associated with the breast shield, which requires the woman to remove her shirt and/or completely expose her breast in order to attach a breast pump device. This, therefore, often requires entering a private room (e.g., a bathroom), and remaining therein until the pumping is complete. In some systems, a collection element is integrated with an element that attaches to a breast, and the entire device is worn under a bra, shirt or other article of clothing. These systems can be bulky, however, and therefore either require a woman to not wear particular types or sizes of clothing (e.g., a bra) while using the system, or wear a larger size or type of clothing (e.g., a bra that has a larger cup size that she might otherwise wear), in order to accommodate the bulky device with the integrated collection element. After removing the device, therefore, a bra may not fit correctly, and therefore may have too much space or otherwise not provide proper support for the woman's breasts. By having a shield that is separate from the collection container, however, the shield may be formed more thinly, and therefore not significantly alter a user's clothing requirements. Furthermore, the woman may discreetly and quickly begin the pumping process in almost any place. For example, she may simply slide the shield into place over her breast, under her bra, by passing it through her collar, her sleeve, or under her shirt or dress. Similarly, when the woman is completed pumping, she may easily and discreetly remove the shield by a same or similar method.

In some embodiments, the shield, the collection container, and or the tubing may be reusable. For example, a woman may use the shield, collection container, and tubing with a breast pump to pump breast milk. After she is finished pumping, the collection container may be sealed and stored with the milk, or the milk may be transferred to another container for storage and later use. In some embodiments, the container may be made of a material that may be frozen. After the milk is removed from the collection container, the collection container may be cleaned and reused. Similarly, after the woman is done pumping, the shield and/or the tubing may be cleaned and reused. For example, depending on the material the shield, tubing, and/or collection container are made of, the shield, tubing, and/or collection container may be cleaned in a dishwasher, microwave, or through another method. For example, the tubing may be cleaned with a syringe, a flush, or another method. For example, the tubing may be immersed in warm soapy water while attached to the pump, the pump activated to pump the soapy water through the tubing, then the tubing immersed in non-soapy water, and the pump activated to pump the non-soapy water through the tubing.

Alternatively, in some embodiments, the shield, tubing, and/or collection container may be disposable. For example, after the woman is done pumping, she may dispose of the shield and/or tubing. Additionally, for example, after the milk is removed from the collection container, the collection container may be disposed of.

In some embodiments, the collection container may include an integrated device for treating breast milk that enters or is in the collection container. For example, the collection container may include an ultraviolet (UV) light source, a pasteurization device (e.g., a heating element), or the like. The treatment device may treat breast milk entering the collection container (e.g., at a portion of the collection container where the tubing (e.g., collection tubing 140) connected to the shield joins the collection container). Alternatively or additionally, the treatment device may treat breast milk at a portion of the collection container that collects the breast milk (e.g., the treatment device may be integrated into a lid, a base, or a wall of the collection container). For example, a UV light source may shine UV light on breast milk that is in the collection container, and/or on breast milk entering the collection container. The treatment device may be triggered or activated by a vacuum- and/or pressure-sensitive switch, which may cause the treatment device to turn on when a vacuum is applied to the system. Alternatively or additionally, the pressure-sensitive switch (e.g., which may be integrated into a base of the collection container) may cause the treatment device to turn on when milk enters or is in the collection container. The treatment device may be configured to turn off after a certain amount of time (e.g., a threshold amount of time after milk has entered the collection container). The treatment device may be independently powered (e.g., by a battery), or may be connected to the pump and/or a power source of the pump.

In some embodiments, the collection container may include an integrated device for heating and/or cooling breast milk that enters or is in the collection container. For example, the collection container may include a heating element and/or a refrigerating or cooling element, which may be used to heat, cool, and/or maintain breast milk at a particular temperature. In some embodiments, the collection container may include one or more temperature sensors. In some embodiments, the collection container may heat and/or cool the milk to maintain the milk at a safe temperature. For example, a computing device connected to or integrated with the collection container may determine, using information from the temperature sensor, that the milk has been at a particular temperature for a threshold period of time (e.g., a maximum safe period of time to leave breast milk at the particular temperature), and initiate cooling of the milk. In some embodiments, the cooling element might not be activated immediately upon the milk entering the bottle, because it may be easier to give room-temperature milk to a baby than cool milk, and therefore it may be desirable to maintain milk at a room temperature for a safe period of time, then cool the milk to safely maintain the milk for a longer usable time period.

FIGS. 18A-18D depict an illustrative embodiment of a collection container (e.g., collection container 1802), which may include one or more aspects described herein. A collection container may include a top section (e.g., 1804). The top section may attach (e.g., screw, suction fit, etc.) onto the collection container. In some embodiments, the top section may be removable or might not be removable from the collection container.

A collection container may include one or more connection points (e.g., connection point 1806, connection point 1808) for attaching tubing. One of the connection points may be attached to one end of tubing that is attached to a pump. Another of the connection points may be attached to one end of tubing that is attached to a breast shield. In some embodiments, if more than two connection points exist, each connection point may be closed (e.g., sealed off) or connected to tubing connected to another part of the system (e.g., there may be two connection points, each with tubing to a respective breast shield, and a third connection point with tubing to a pump). This may allow for a closed or sealed system, such that suction may be created by the pump.

A collection container may include valve opening 1810. Valve opening 1810 may be covered by a movable flap or valve (e.g., a silicone valve), which may open to allow air to exit from the collection container, and close as suction is created by the pump. For example, as a breast pump operates, it may cyclically create suction by sucking air through the pump tubing, which may travel through the pump tubing, through the collection container—the valve of which may be sucked closed—through the collection tubing, into the breast shield, and may suck the nipple into the breast shield to extract milk from the nipple. When the pump cyclically releases the suction, the valve may open to allow a release of air from the collection container. Milk from the nipple may flow through the breast shield, through the collection tubing, into the collection container. In some embodiments, because the valve opening may be near the connection points of the collection container, milk may more easily flow from the breast shield, through the tubing, into the collection container, without being impacted or slowed by the cyclical suction created by the pump.

Returning to FIG. 1, the tubing (e.g., collection tubing 140 and/or pump tubing 150) may be a tubing that connects the pump to the collection container, and the collection container to the shield. According to at least one embodiment, the tubing may be flexible tubing. Alternatively, the tubing may be rigid. In some embodiments, the tubing may be clear. Alternatively, the tubing may be opaque or colored. In some embodiments, the tubing may change color (e.g., the tubing may be reactive) when liquid flows through the tubing, which may provide a visual indication that liquid (e.g., milk) is flowing inside. In some embodiments, the tubing may be of a similar diameter to channel 12 (channel 12 may be part of the breast shield, and is discussed in more detail below). In some embodiments, the tubing may be a different diameter than channel 12. In some embodiments, the tubing may be made of one or more of vinyl, silicone, urethane, polypropylene, or another food-safe material. The tubing may be made of hydrophobic polymers. For example, this may allow for more easy or quick drying of the tubing after the tubing is used and/or cleaned. In some embodiments, the tubing may be made of one or more of the above-mentioned materials, and may be coated in a food-safe hydrophobic material (e.g., Liquiglide), which may create a permanent slippery surface to which milk might not stick. This may help reduce and/or eliminate waste of milk in the tubing, and/or make for easier cleaning and/or sanitation of the tubing.

In some embodiments, the collection tubing may be at least six inches long, at least 12 inches long, at least 18 inches long, at least 24 inches long, or another length. In some embodiments, the pump tubing may be at least six inches long, at least 12 inches long, at least 18 inches long, at least 24 inches long, or another length.

In some embodiments, the tubing may be connected to the breast shield directly. In other embodiments, the tubing may be connected to the breast shield via a connector (e.g., connector 160). The connector may have one or more ends to connect to the breast shield, and one or more ends to connect to the tubing. For example, the connector may have one end to connect to the breast shield, and one end to connect to tubing that connects to a collection container. Alternatively, the connector may have an end that connects to the breast shield, and an internal splitter that connects the end that connects to the breast shield to multiple ends that each connect to tubing to provide milk to multiple collection containers.

In some embodiments, the connector may be straight. In some embodiments, the connector may be angled or curved. In some embodiments, the connector may be made of a hard and/or rigid material. In some embodiments, the connector may be made or a soft, pliable, and/or flexible material. The connector may made of a material that allows for a tight seal between the connector and the shield and for a tight seal between the connector and the tubing, which may allow for a vacuum to be maintained within the breast pump device when the pump is operated.

In some embodiments, the connector may have a first diameter on an end that mates with the tubing, and a second, different diameter on an end that mates with channel 12. Thus, in some embodiments, a tubing that is a different diameter than a diameter of channel 12 may be used with the breast shield.

In other embodiments, the connector (e.g., connector 160) may be a same diameter on an end that mates with the tubing and on an end that mates with the breast shield. Thus, the connector may be used with tubing that is a same diameter as channel 12.

In some embodiments, the connector may have a male connection for connecting with the tubing. In some embodiments, the connector may have a female connection for connecting with the tubing. In some embodiments, the connector may have a male connection for connecting with the breast shield. In some embodiments, the connector may have a female connection for connecting with the breast shield.

In some embodiments, one or more of the shield, collection container, and/or tubing may be made in whole or in part of, treated with, coated with, and/or lined with an antimicrobial material (e.g., silver-impregnated material). For example, one or more of the shield, the collection container, and/or the tubing may lined or coated with silver-impregnated silicone foam. Alternatively or additionally, copper and/or copper alloys (e.g., brass, bronze, cupronickel, copper-nickel-zinc) may be antimicrobial materials that could be used for treating and/or manufacturing one or more of the shield, collection container, and/or tubing.

In some embodiments, a tubing attachment may include a sanitation device (e.g., a UV light), which may be attached to the tubing and activated for drying and/or sanitizing the tubing after using and/or washing the tubing.

A breast shield may interoperate with one or more pre-existing breast pump systems. For example, the breast shield may be used with a pre-existing pump system, which may have, for example, one or more of a pump, tubing, and/or collection container. For example, a pre-existing pump system may be manufactured and/or sold by or as MEDELA, AMEDA, PLAYTEX, GERBER, AVENT, EVENFLO, or the like. The tubing of the pre-existing pump system may be used (e.g., by direct connection to channel 12 or via connector 160) to connect to the breast shield (e.g., shield 110). The breast shield (e.g., shield 110) may be used in place of a shield or other mechanism by which a pre-existing pump system attaches to a breast, to allow for the benefits of the breast shield (e.g., the benefits discussed herein), without a user having to purchase or replace the tubing, pump, or collection container of a pump system that the user may already own or otherwise have access to. In some instances, a breast shield and/or connector may be manufactured and sold without a collection container, tubing, and/or pump.

FIGS. 2-7 show different views of one illustrative embodiment of a breast shield (e.g., breast shield 200) for use with a breast pump device. In some embodiments, breast shield 200 may be similar to breast shield 110 depicted in FIG. 1.

FIGS. 16A-16E show different views of one illustrative embodiment of a breast shield (e.g., breast shield 1600) for use with a breast pump device. In some embodiments, breast shield 1600 may be similar to breast shield 110 depicted in FIG. 1.

FIGS. 17A-17F show different views of one illustrative embodiment of a breast shield (e.g., breast shield 1700) for use with a breast pump device. In some embodiments, breast shield 1600 may be similar to breast shield 110 depicted in FIG. 1.

Figure 2:
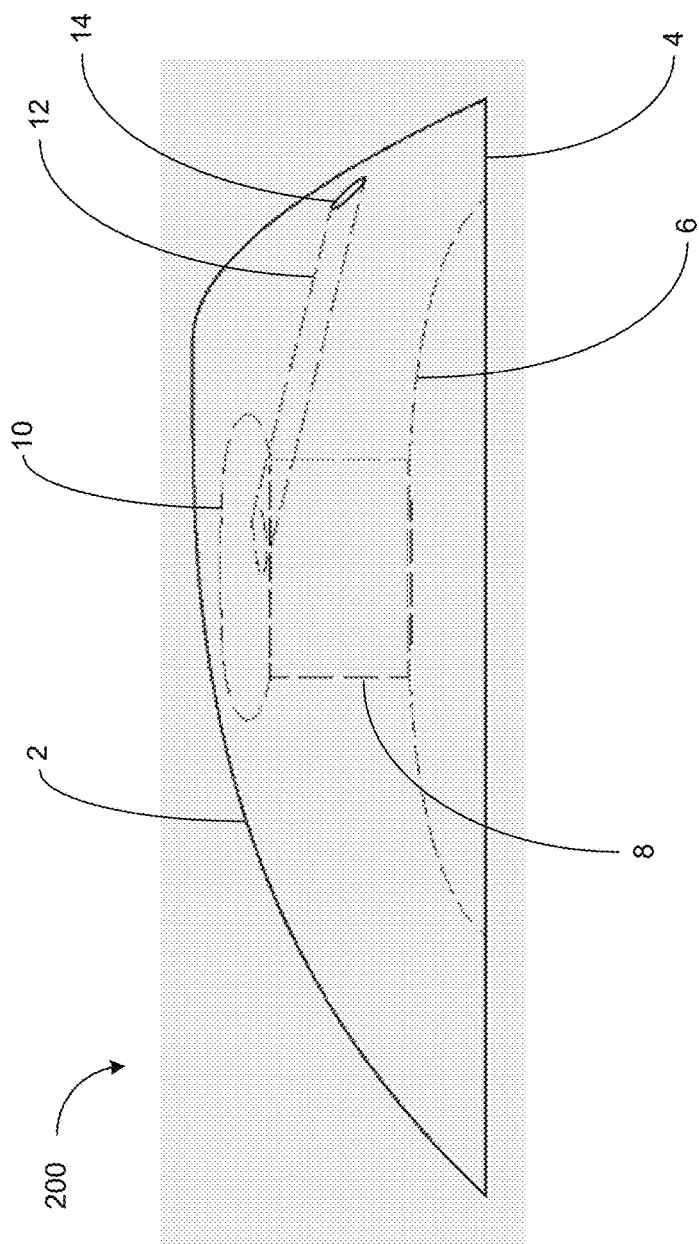
FIG. 2 is a perspective side view of a breast shield according to at least one embodiment described herein.
Figure 3:
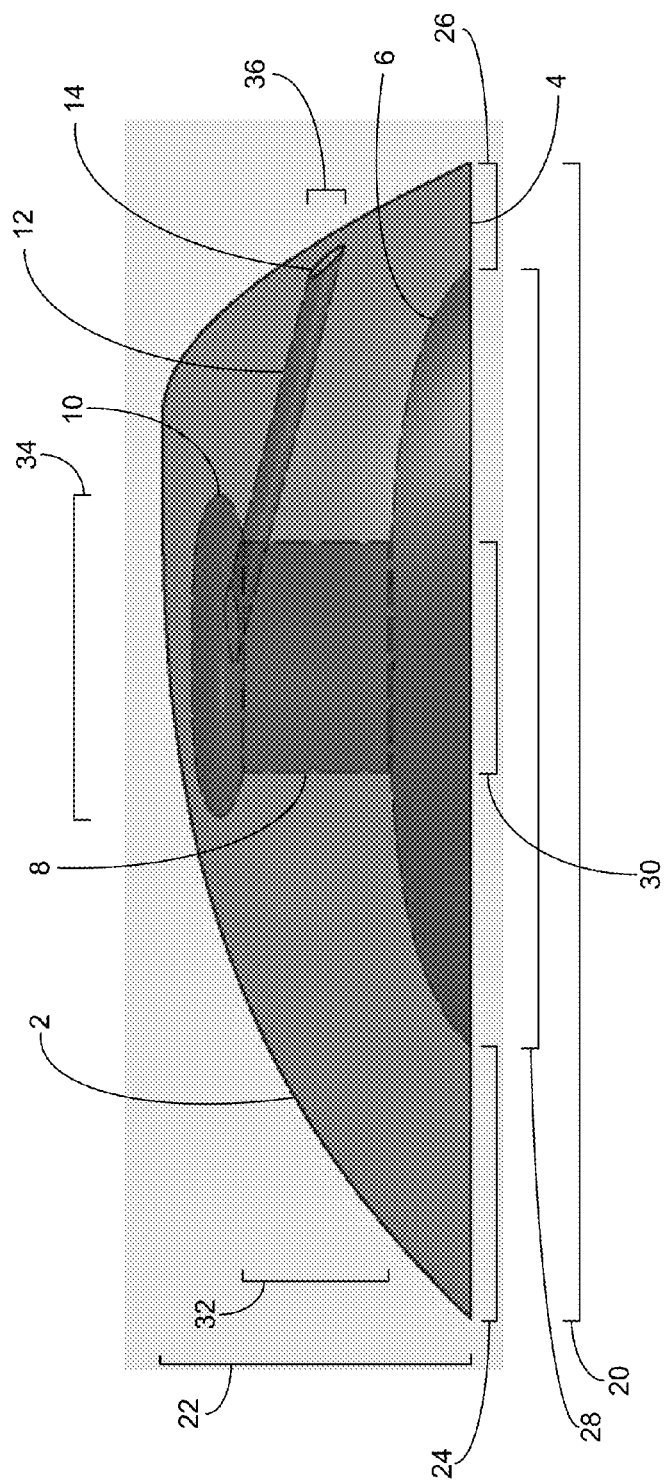
FIG. 3 is a perspective side view of a breast shield according to at least one embodiment described herein.
Figure 4:
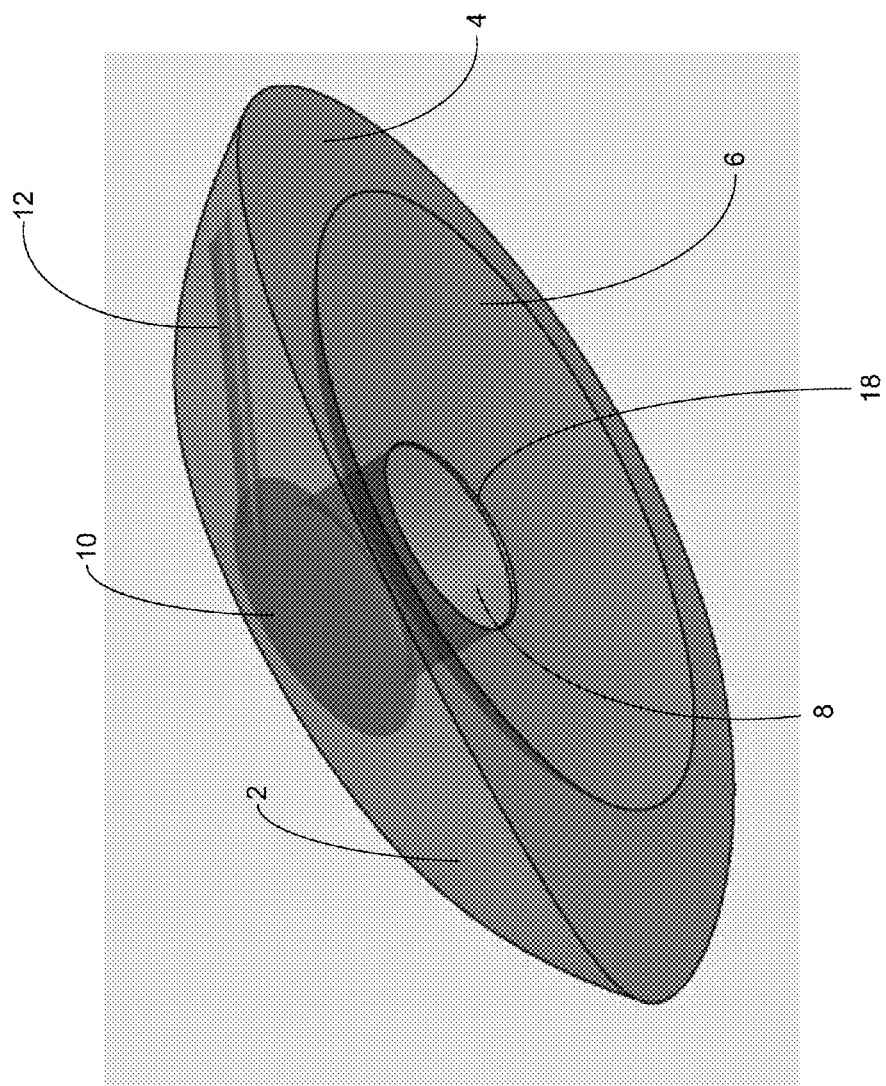
FIG. 4 is an oblique perspective view of a breast shield according to at least one embodiment described herein.
Figure 5:
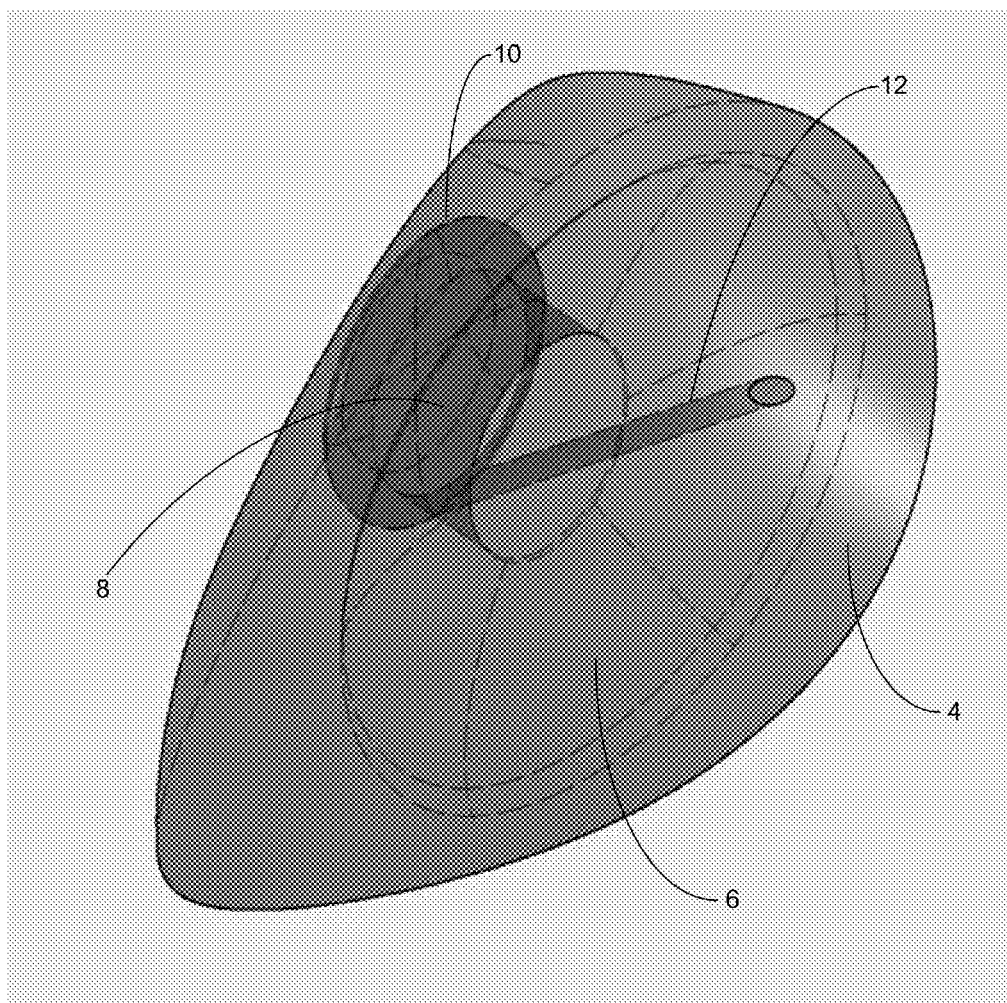
FIG. 5 is an oblique perspective view of a breast shield according to at least one embodiment described herein.
Figure 6:
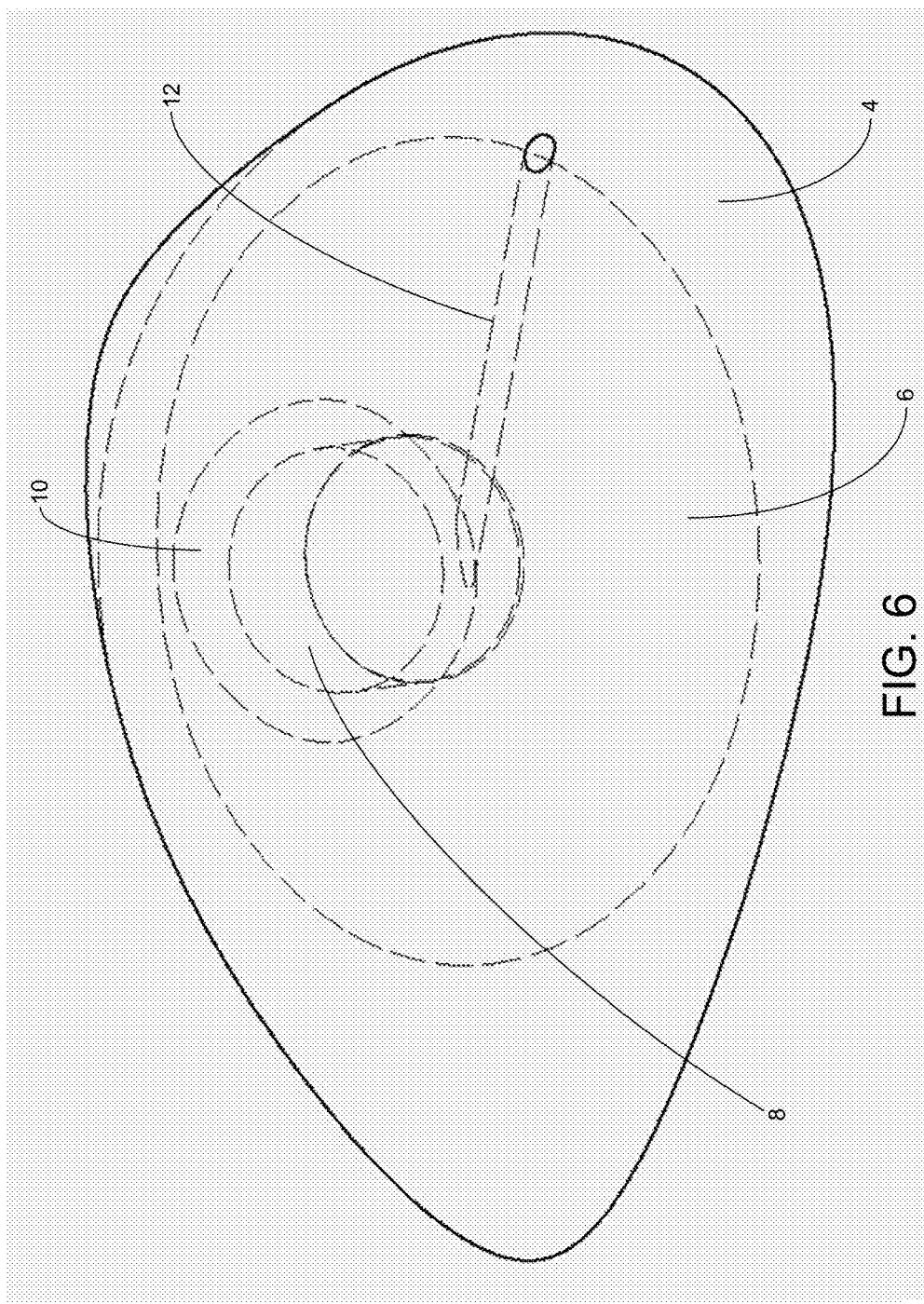
FIG. 6 is an oblique perspective view of a breast shield according to at least one embodiment described herein.
Figure 7:
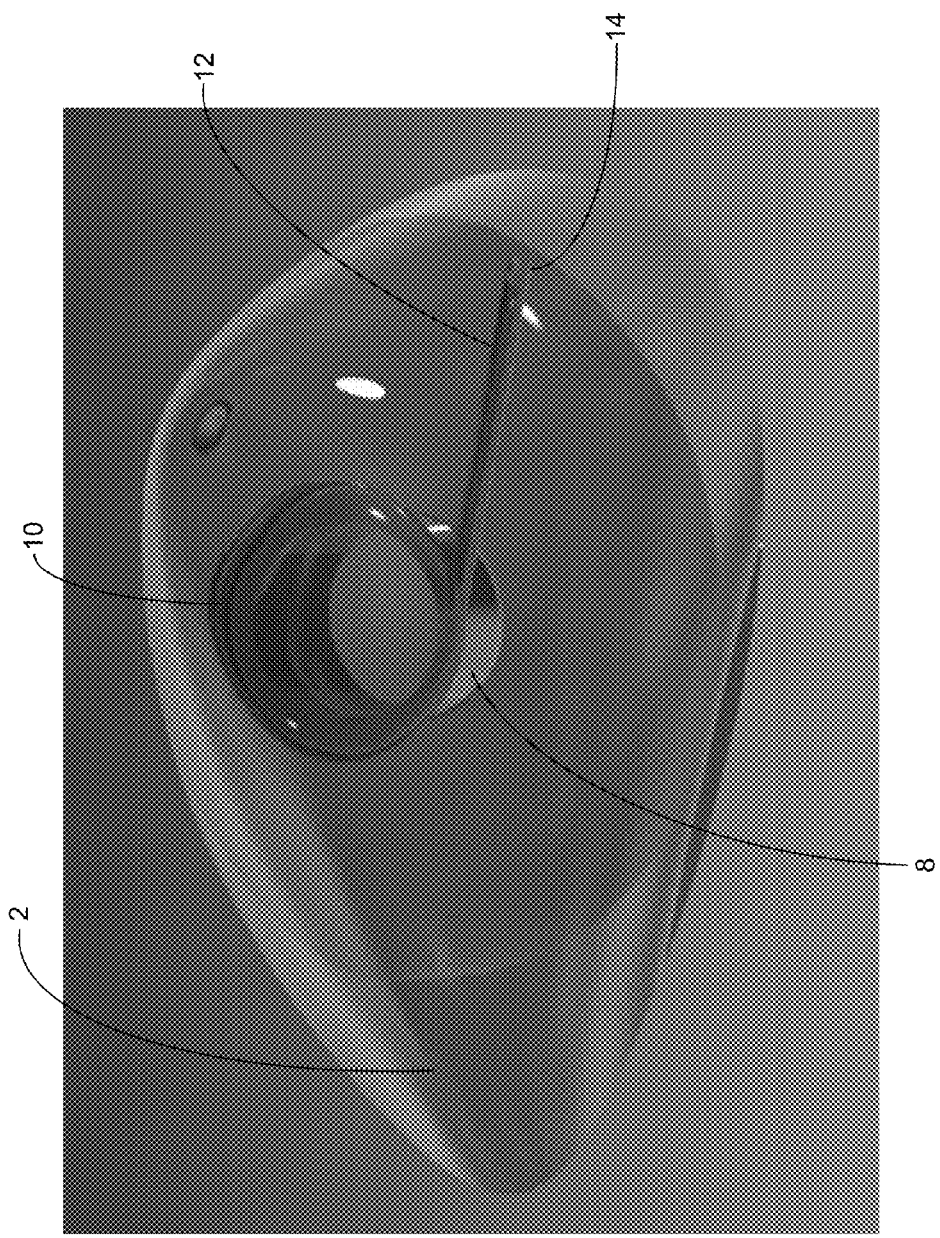
FIG. 7 is a perspective top view of a breast shield according to at least one embodiment described herein.

FIG. 2 is a perspective side view of one embodiment of a breast shield that may be used as part of a breast pump device. FIG. 3 is a perspective side view of one embodiment of a breast shield that may be used as part of a breast pump device. FIG. 4 is an oblique perspective view of one embodiment of a breast shield that may be used as part of a breast pump device. FIG. 5 is an oblique perspective view of one embodiment of a breast shield that may be used as part of a breast pump device FIG. 6 is an oblique perspective view of one embodiment of a breast shield that may be used as part of a breast pump device. FIG. 7 is a perspective top view of one embodiment of a breast shield that may be used as part of a breast pump device.

Breast pump shield 200 may be attached to a woman's breast relative to an in-use orientation. If the woman is upright relative to the ground (e.g., the woman is standing up on the ground), the in-use orientation may include an upward direction away from the ground, a downward direction toward the ground, a leftward direction toward the woman's left hand, and a rightward direction toward the woman's right hand.

As illustrated in FIGS. 2-7, breast pump shield 200 may include a concave interior surface (e.g., interior portion 6), a convex exterior surface (e.g., exterior portion 2), and a connecting surface (e.g., middle portion 4) that connects the concave interior surface with the convex exterior surface. Interior portion 6 may be a surface that receives and contacts a breast when breast pump shield 200 is worn. Exterior portion 2 may be a surface on another side of interior portion 6 that forms an outer surface of breast pump shield 200 when breast pump shield 200 is worn. Middle portion 4 may be a connecting surface between the concave interior portion and the convex exterior portion, such that middle portion 4 contacts an area around a breast when breast pump shield 200 is worn.

In some embodiments, a shield may be smaller than an entire breast (e.g., the shield may cover only a part of the breast, including the nipple). When suction is applied, a portion of or the entire shield may compress the nipple to extract milk from the nipple.

Breast pump shield 200 may be manufactured in different predetermined sizes to fit different size breasts. For example, interior portion 6, exterior portion 2, and middle portion 4 may be different dimensions, based on a size of the breasts of the woman who is using breast pump shield 200. For example, breast pump shield 200 may be manufactured in sizes corresponding to standard bra sizes (e.g., cup size A, B, C, D, DD, E). In another example, breast pump shield may be manufactured in extra-small, small, medium, large, and extra-large sizes, or the like. In some embodiments, breast pump shield 200 may be sized based on different breast and/or nipple sizes, but might not correspond to cup sizes. For example, breast pump shield 200 may be significantly thinner than, for example, a breast insert of a particular cup size (e.g., a DD-size breast insert may be thicker than a breast pump shield designed for a woman with DD-size breasts). Instead, breast pump shield 200 may have a larger or smaller overall diameter, length, or other dimension, which may result in a larger or smaller interior concave surface area (e.g., interior portion 6) to accommodate a larger or smaller breast, but a breast pump shield 200 designed for a larger breast might not have a significantly greater thickness (e.g., thickness 22) than a breast pump shield 200 designed for a smaller breast.

As shown in FIG. 3, a longest part of exterior portion 2 may have a length 20. A greatest thickness of exterior portion 2 (e.g., from a plane of a face of middle portion 4 to a parallel plane at an outermost part of exterior portion 2) may have a thickness 22. A longest part of an opening in middle portion 4 to form a largest diameter of interior portion 6 may have a longest diameter 28. Interior portion 6 may be circular (e.g., interior portion 6 has a longest diameter 28, which may be a diameter that is a same length when measured in any direction on the plane of the face of the middle portion 4). Alternatively, interior portion 6 may be oval (e.g., longest diameter 28 is longer than a different diameter measured in a different direction on the plane of the face of the middle portion 4). A part of middle portion 4 that contacts a first area around a breast may be a first length 24, and a second part of middle portion 4 that contacts a second area around a breast may be a second length 26. In some embodiments, first length 24 may be different from second length 26. Alternatively, first length 24 may be the same as second length 26.

In some embodiments, thickness 22 may be less than length 20. For example, a ratio of thickness 22 to length 20 may be one of 2:1, 3:1, 4:1, or another ratio. Thickness 22 may be within a range in relation to length 20 (e.g., length 20 may be greater than two times thickness 22, length 20 may be greater than two times thickness 22 but less than three times thickness 22, length 20 may be greater than three times thickness 22, length 20 may be greater than three times but less than four times thickness 22, length 20 may be greater than four times thickness 22, or the like). Thus, by having a thickness 22 that is less than length 20 (e.g., length 20 is greater than two, three, four, etc., times thickness 22), the shield may be a low-profile shield. This may allow for a woman to easily insert the shield under her clothing (e.g., under a bra that properly fits the woman's breasts without the shield inserted), pump breast milk, and remove the shield, all without having to remove and/or change her shirt or other clothing (e.g., due to clothing size issues). This may be advantageous over other systems that must have a greater thickness so as to accommodate, for example, a collection element that is thick enough to collect all the milk pumped during a pumping session, and as a result, either stretch out a woman's bra or other clothing, or require her to wear a larger-than-otherwise-required bra that might not fit properly when the device with the integrated collection container is removed.

Alternatively, thickness 22 may be equal to or greater than length 20. For example, breast pump shield 200 may integrated into a breast enlargement insert, which may be inserted into a bra to give the wearer the appearance of having larger breasts.

In some embodiments, breast pump shield 200 may be custom-made to fit a particular woman's breast. For example, each of a woman's breasts may be measured (e.g., using a laser, measuring tape, a three-dimensional scan, molding, or other method) to determine the dimensions of the woman's breasts. A pair of breast pump shields 200 may be manufactured so that the dimensions of each breast pump shield 200 (e.g., dimension of interior portion 6, exterior portion 2, and middle portion 4) allow for each breast pump shield 200 to fit each of the woman's breasts. In some embodiments, breast shield 200 may be manufactured using a three-dimensional printing process, based on the measurements of the intended user's breasts, to allow for a precise fit of breast pump shield 200.

For example, at least three elements of the shield may be customized for an individual. First, the exterior convex curve (e.g., exterior portion 2) may be customized to provide a desired aesthetic of the shield. Second, the nipple shield (e.g., chamber 8) may be customized to allow for a particular nipple morphology and excursion. For example, the nipple shield may be tapered to be thinner or thicker, and/or deeper or shallower. Third, the conformal concave structure (e.g., interior portion 6) may be customized to provide sufficient surface area for a good suction fit. Each of these three elements may be independently varied, which may allow for a custom fit shield.

Alternatively or additionally, an exterior may be customized with different colors, shapes, designs, patterns, or the like.

In some embodiments, breast pump shield 200 may be shaped to fit a right breast. In some embodiments, breast pump shield 200 may be shaped to fit a left breast. In some embodiments, breast pump shield 200 may be shaped to fit either a right or left breast.

In some embodiments, breast pump shield 200 may be formed in a circular shape. In some embodiments, breast pump shield 200 may have a teardrop or other asymmetrical shape. For example, when the breast pump shield 200 is attached to a woman's breast according to the in-use orientation described above, a largest width in a left-right direction of an upper half of breast pump shield 200 may be smaller than a largest width in a left-right direction of a lower half of breast pump shield 200. For example, breast pump shield 200 may appear in a tear drop shape over the woman's breast, with the smaller portion of the tear drop closer to the woman's neck, and the wider portion of the tear drop closer to the woman's feet.

In some embodiments, interior portion 6 and/or middle portion 4 may be made of or lined with a material to allow for breast pump shield 200 to maintain contact with a woman's breast. For example, interior portion 6 and/or middle portion 4 may be made of a material or lined with a reusable adhesive that adheres to or creates friction with skin.

Breast pump shield 200 may further comprise a chamber 8. Chamber 8 may be configured to extend from a portion of interior portion 6 toward exterior portion 2. Chamber 8 may be configured such that a nipple lies within chamber 8 when breast pump shield 200 is attached to the breast.

In some embodiments, similar to the above discussion (in relation to interior portion 6, exterior portion 2, and middle portion 4), chamber 8 may be manufactured in different sizes to correspond to different size nipples. In some embodiments, breast pump shield 200 may be manufactured with different predetermined sizes of chamber 8 (e.g., small, medium large). In some embodiments, breast pump shield 200 may be manufactured with a size of chamber 8 being based on custom measurements of an intended user. For example, a three-dimensional printing process may be used to manufacture breast pump shield 200, which may allow for the size of chamber 8 to be based on custom measurements of a nipple of the intended user. In some embodiments, altering a size of chamber 8 might not alter an overall size of breast pump shield 200 (e.g., a size of exterior portion 2), or a size of another portion (e.g., interior portion 6 or middle portion 4) of breast pump shield 200. This is because a nipple size may vary independent of breast size (e.g., a woman with small breasts may have large nipples, a woman with small breasts may have small nipples, a woman with large breasts may have small nipples, a woman with large breasts may have large nipples, and the like). Therefore, in order to provide a more effective breast pump shield (e.g., to ensure that breast pump shield 200 fits properly, creating a good seal, which may allow for sufficient suction to be created within the breast pump device or system), a dimension of chamber 8 may be varied independently from a dimension of a different portion of breast pump shield 200.

In some embodiments, chamber 8 may be orthogonal in relation to a plane of a face of middle portion 4. In some embodiments, a central axis of chamber 8 may be orthogonal to the plane of the face of middle portion 4. In some embodiments, chamber 8 may be oblique in relation to the plane of the face of the middle portion 4. In some embodiments, a central axis of chamber 8 may be oblique (e.g., at a 90 degree angle) in relation to the plane of the face of the middle portion 4. For example, in some embodiments, chamber 8 may be configured such that when breast shield 200 is attached to a breast, and a user is upright in relation to the ground, chamber 8 is inclined at a downward angle (e.g., a portion of chamber 8 closer to interior portion 6 is higher from the ground than a portion of chamber 8 closer to reservoir 10). Thus, when the pump is operated and milk flows from the nipple within chamber 8—assuming the user is in an upright position relative to the ground—gravity may cause milk to flow downward (e.g., toward the ground) through chamber 8 toward reservoir 10 and/or channel 12. Alternatively or additionally, when suction is applied to breast pump shield 200 by an attached pump, the suction may cause milk to flow from chamber 8 to reservoir 10.

Figure 16A:
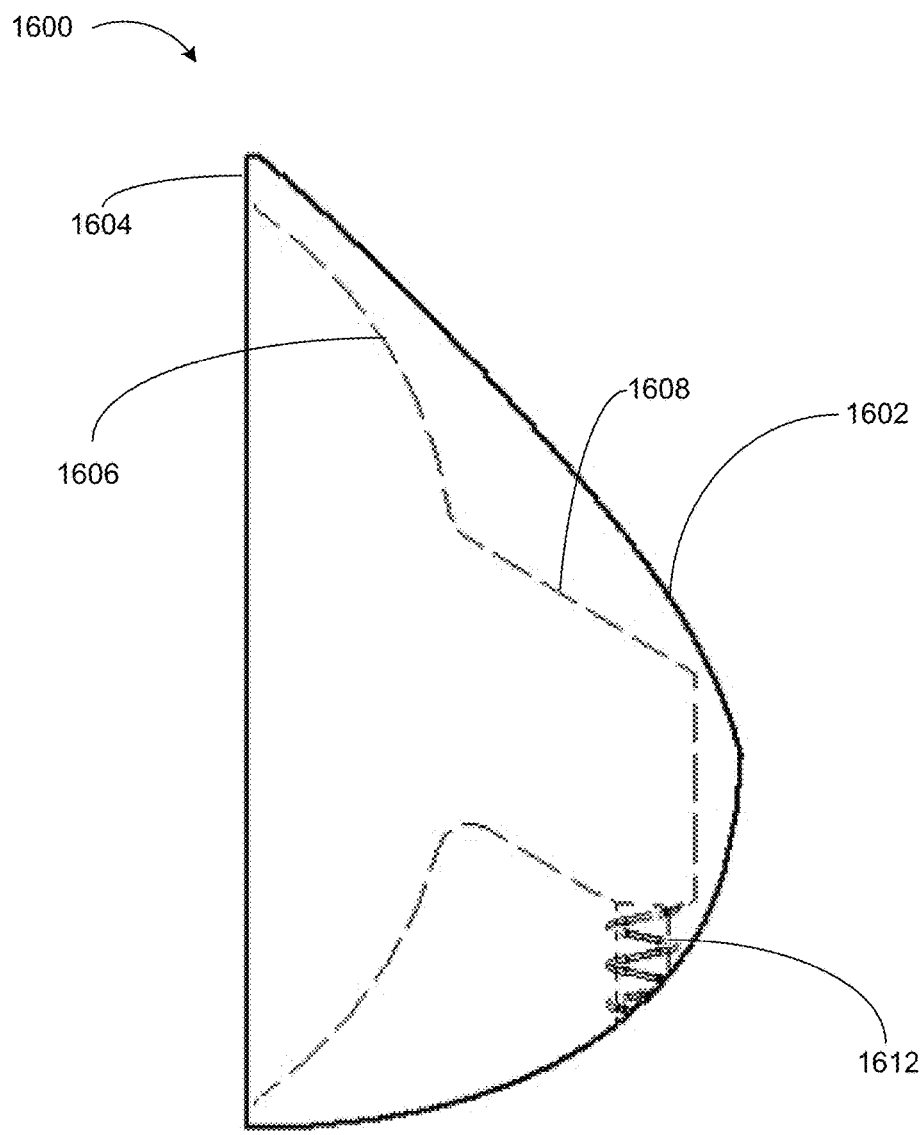
FIG. 16A depicts a lateral perspective view of a breast shield according to at least one embodiment described herein.
Figure 16B:
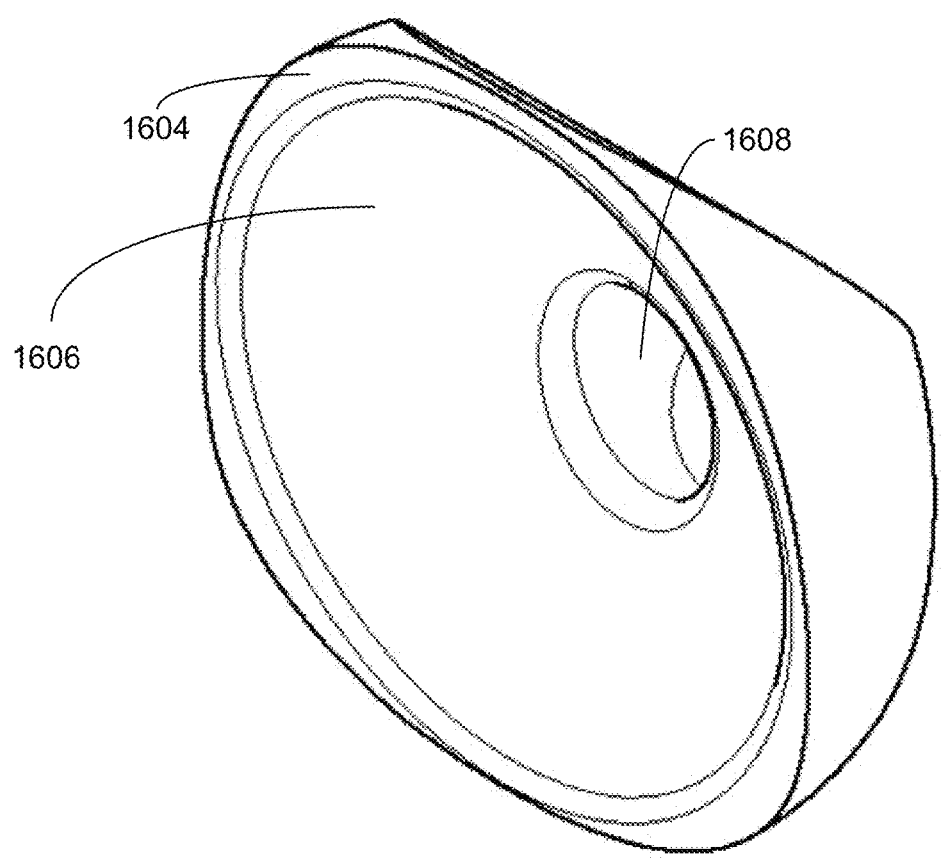
FIG. 16B depicts a posterior superior oblique perspective view of a breast shield according to at least one embodiment described herein.

FIG. 16A depicts an illustrative example of a one embodiment of a breast shield (e.g., shield 1600) with a channel (e.g., channel 1608) that is at an angle relative to an interior concave surface of the breast shield. A central axis of channel 1608 may be at a 45 degree angle relative to a direction orthogonal to a surface parallel to a posterior face (e.g., a face contacting a woman's chest) of shield 1600.

Returning to FIG. 3, in some embodiments, a diameter of chamber 8 may be diameter 30 (e.g., 21 mm, 24 mm, 27 mm, 30 mm, 36 mm, or the like). In some embodiments, a diameter of chamber 8 may be less than longest diameter 28 of interior portion 6.

Chamber 8 may have a length 32 between an end of chamber 8 that is closer to interior portion 6 and an end of chamber 8 that is closer to reservoir 10. For example, in some embodiments, length 32 of chamber 8 may be 45 mm, less than 45 mm, 20 mm, greater than 20 mm, or the like. In some embodiments, a length of chamber 8 may be selected based on a material that chamber 8 is made from (e.g., chamber 8 may be lengthened or shortened so as to avoid causing pain when a nipple is compressed against or into chamber 8).

In some embodiments, chamber 8 may be cylindrical, with a first end having a same diameter as a second end. In some embodiments, chamber 8 may be narrower at a first end than at a second end. For example, at an end closer to interior portion 6, chamber 8 may be a larger diameter than at an end closer to reservoir 10. In some embodiments, chamber 8 may be a round cylindrical shape. In other embodiments, chamber 8 may be an oval cylindrical shape.

In some embodiments, a gasket, ring, or other insert may be attached to one or more of the middle portion, the interior portion, and the chamber. The gasket, ring, or other insert may be made of rubber, silicone, urethane, polypropylene, or another material. In some embodiments, the gasket, ring, or other insert may be made of a porous material and/or a material with multiple holes. In some embodiments, the gasket, ring, or insert may be comfortable for the woman using the shield when the nipple is compressed against the gasket, ring, or insert. The gasket or ring may create an improved seal against the breast when the breast pump shield is attached to the breast.

In some embodiments, the chamber may include a ring or insert within the chamber. For example, an illustrative embodiment of a breast shield (e.g., breast shield 1700) with an insert (e.g., insert 1740) is depicted in FIGS. 17A-17F. In some embodiments, the insert may have rounded edges or flat edges. In some embodiments, the insert may be shaped similar to the shape of a baby's mouth on a side of the insert that contacts the nipple, such that when suction is applied to the interior portion of the chamber (e.g., through the channel), causing the nipple within the chamber to be extended within the chamber, the portion of the insert shaped like a baby's mouth contacts a portion of the nipple, while another portion of the nipple extends into the insert to release milk. In some embodiments, the insert (e.g., insert 1740) may be shaped similar to a thimble, and may include a hole in an end of the insert (e.g., near a tip of the insert). In this manner, an efficiency and/or comfort of the breast pump system may be improved. Specifically, most breast pump systems work based on suction (e.g., by applying a suction to air within a sealed system, the breast pump causes a nipple to be stretched within a chamber (e.g., chamber 1608 of breast shield 1600), and the stretching causes the nipple to release milk). By including the insert within the chamber (e.g., chamber 1708), when the suction is applied to the sealed system within the breast pump shield, the nipple may be extended toward the insert and compressed against the insert. A majority or all of a surface of the nipple may be compressed against the insert, and the suction may cause the insert to squeeze the nipple like a sponge. Milk may be extracted from the nipple and exit the insert through a hole in the end of the insert, without the nipple being fully stretched out. Thus, the breast pump may more closely simulate a natural breast-feeding experience, which may result in an improved efficiency with regard to pumping milk, as well as a more comfortable experience for the woman.

Returning to FIG. 2, breast pump shield 200 may include a reservoir 10. Reservoir 10 may extend from a portion of interior portion 6 toward an exterior portion 2. Reservoir 10 may temporarily collect milk that is pumped from a nipple within chamber 8 when breast pump shield 200 is attached to a breast. Reservoir 10 may prevent back flow, and allow the milk to be funneled into the channel (e.g., channel 12).

In some embodiments, a largest diameter of reservoir 10 may be diameter 34 (e.g., 22 mm, 23 mm, 25 mm, 26 mm, 28 mm, 29 mm, 31 mm, 33 mm, 37 mm, 38 mm, or the like). Diameter 34 may be larger (e.g., 1-2 mm larger) than diameter 30 of chamber 8. In some embodiments, diameter 34 may be a same diameter as diameter 30 of chamber 8. In some embodiments, diameter 34 may be a smaller diameter as diameter 30 of chamber 8.

Figure 16C:
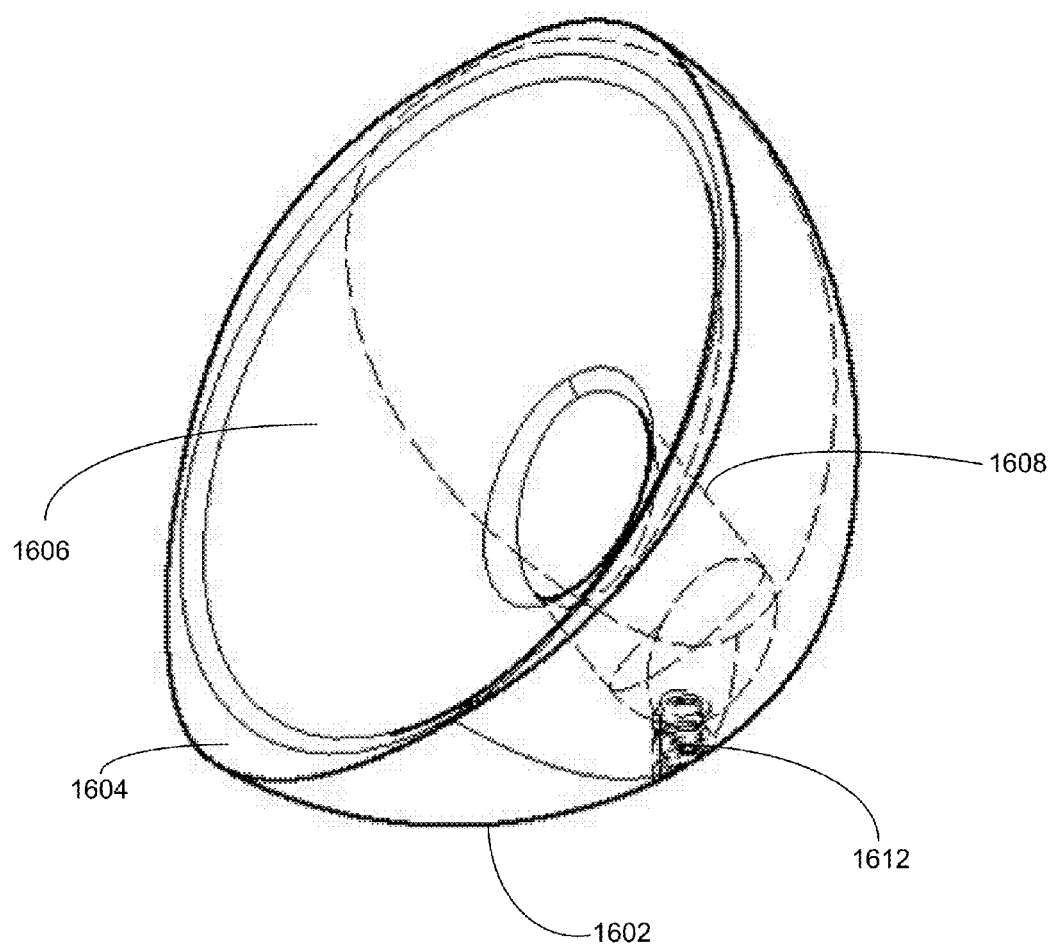
FIG. 16C depicts a posterior oblique perspective view of a breast shield according to at least one embodiment described herein.
Figure 16D:
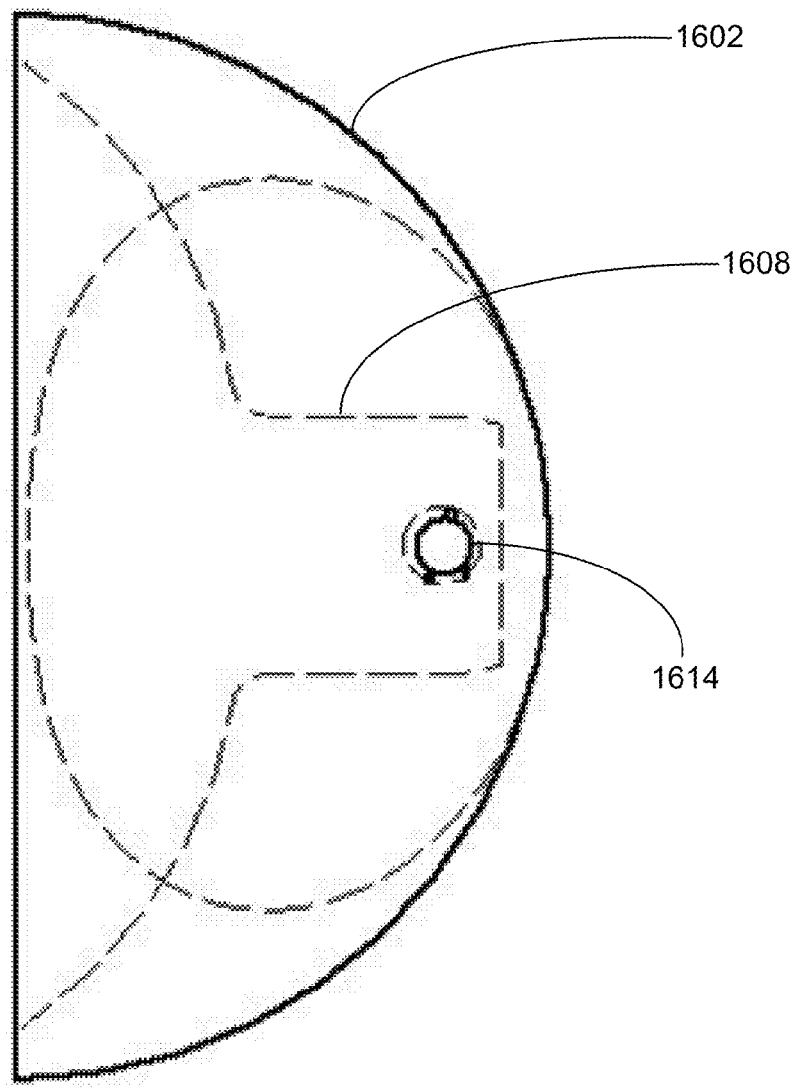
FIG. 16D depicts an inferior perspective view of a breast shield according to at least one embodiment described herein.
Figure 16E:
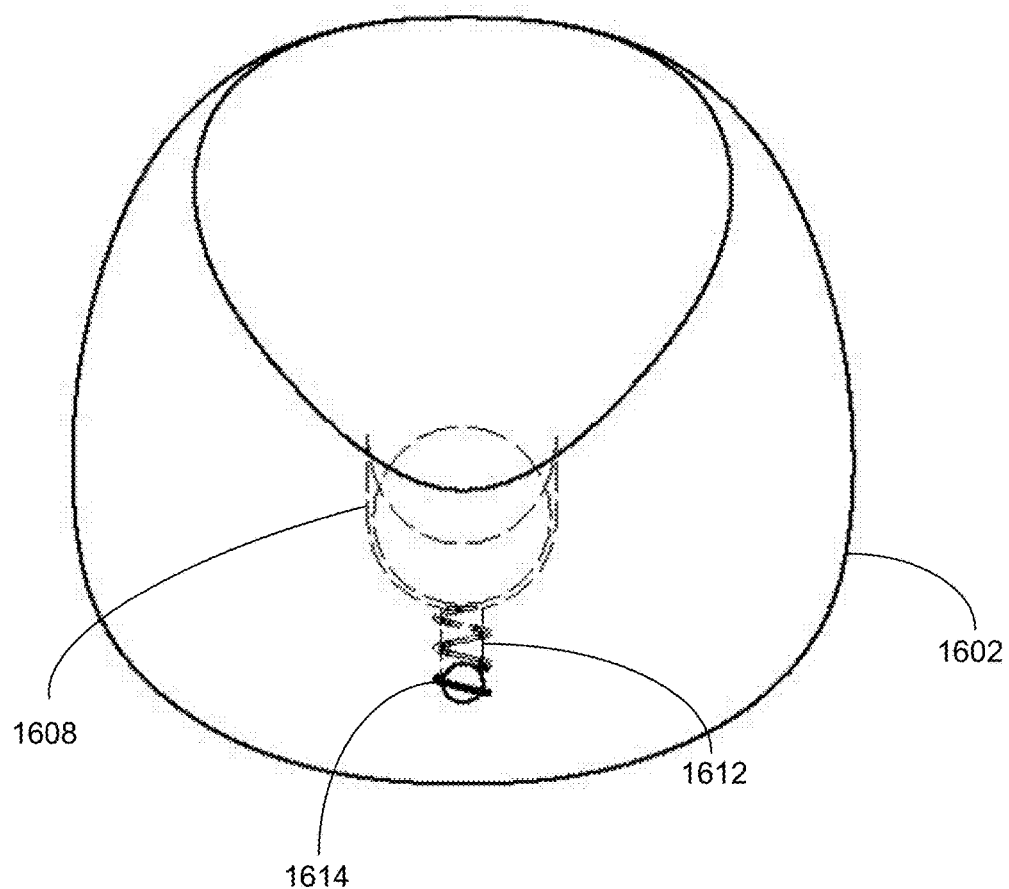
FIG. 16E depicts a front perspective view of a breast shield according to at least one embodiment described herein.
Figure 17A:
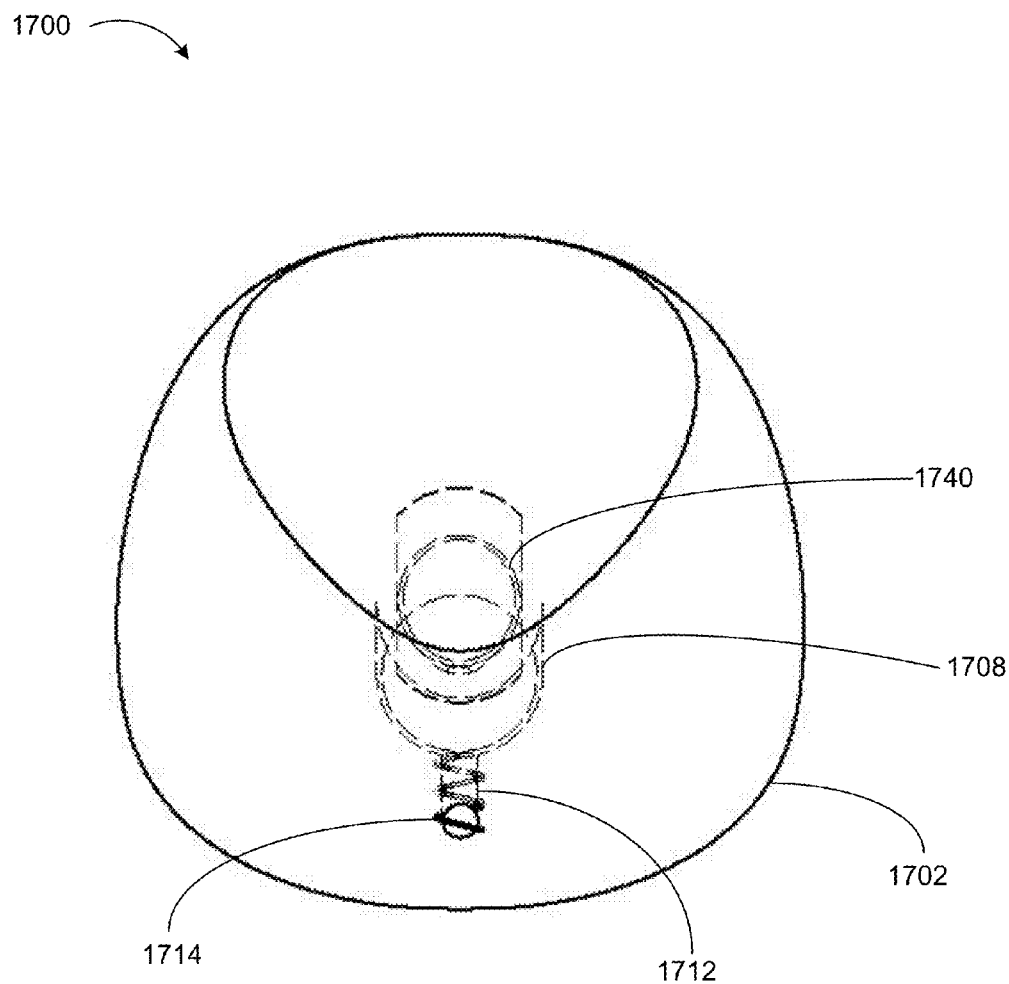
FIG. 17A depicts an anterior perspective view of a breast shield according to at least one embodiment described herein.
Figure 17B:
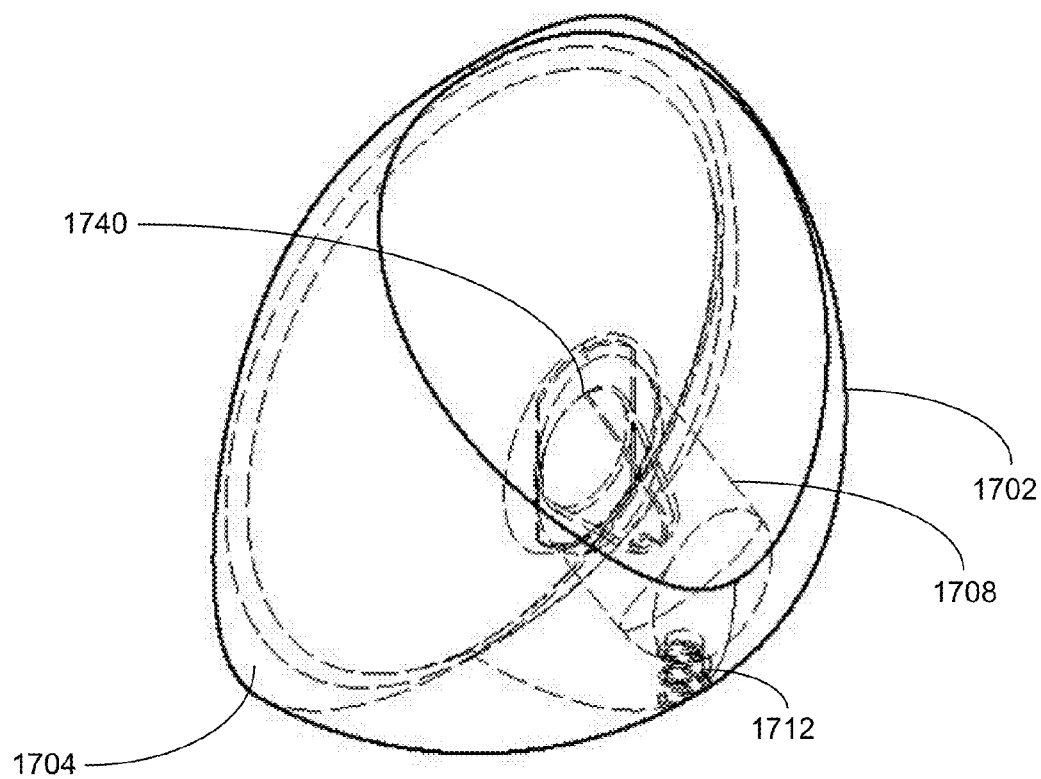
FIG. 17B depicts an anterior oblique perspective view of a breast shield according to at least one embodiment described herein.
Figure 17C:
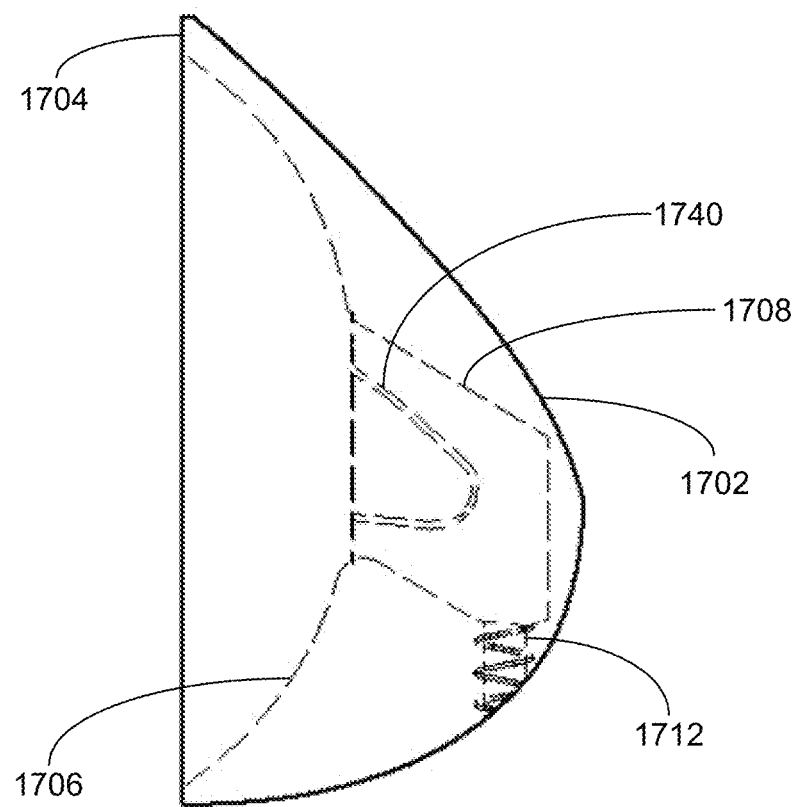
FIG. 17C depicts a lateral perspective view of a breast shield according to at least one embodiment described herein.
Figure 17D:
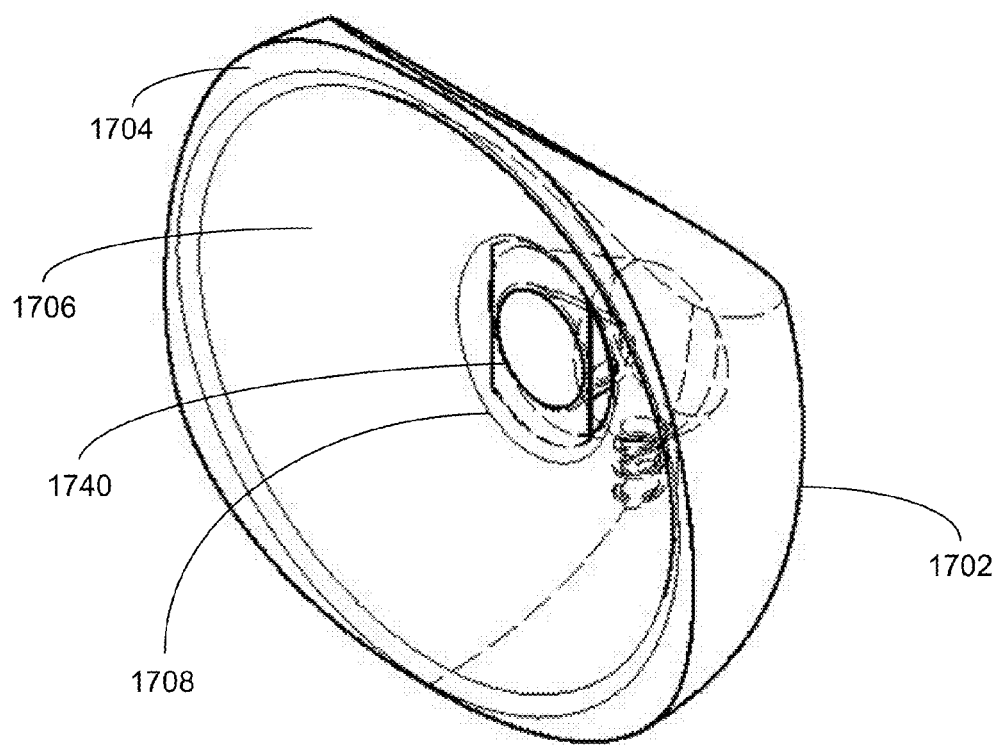
FIG. 17D depicts a posterior oblique perspective view of a breast shield according to at least one embodiment described herein.
Figure 17E:
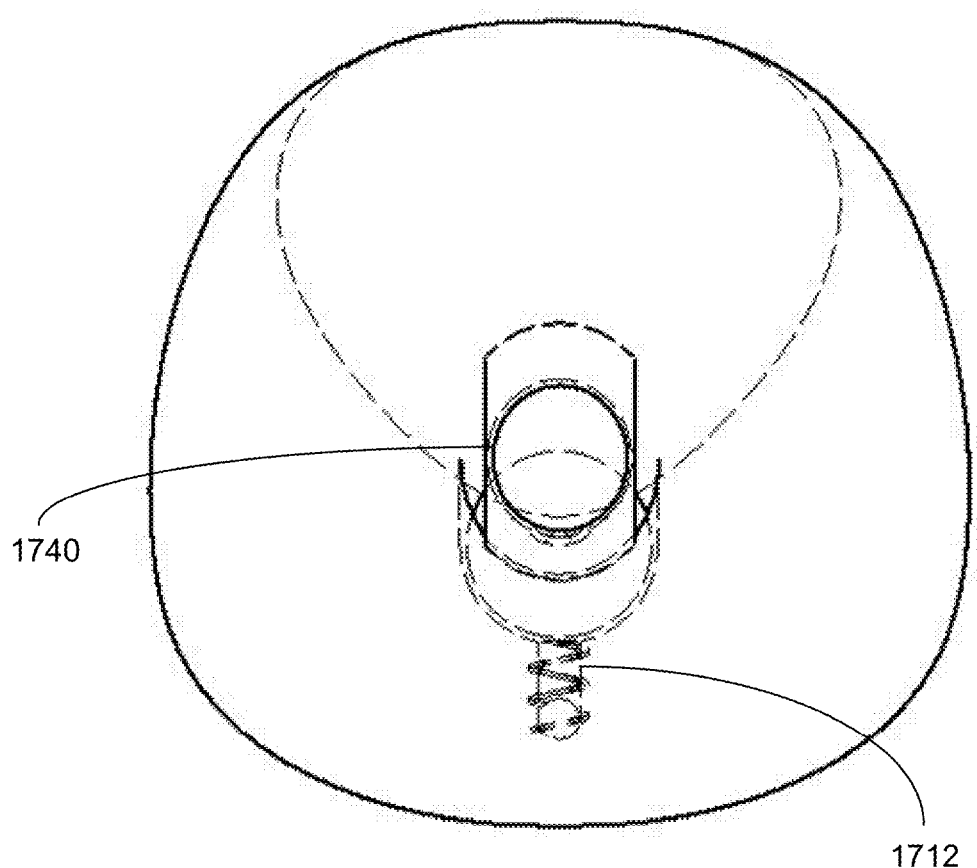
FIG. 17E depicts a posterior perspective view of a breast shield according to at least one embodiment described herein.
Figure 17F:
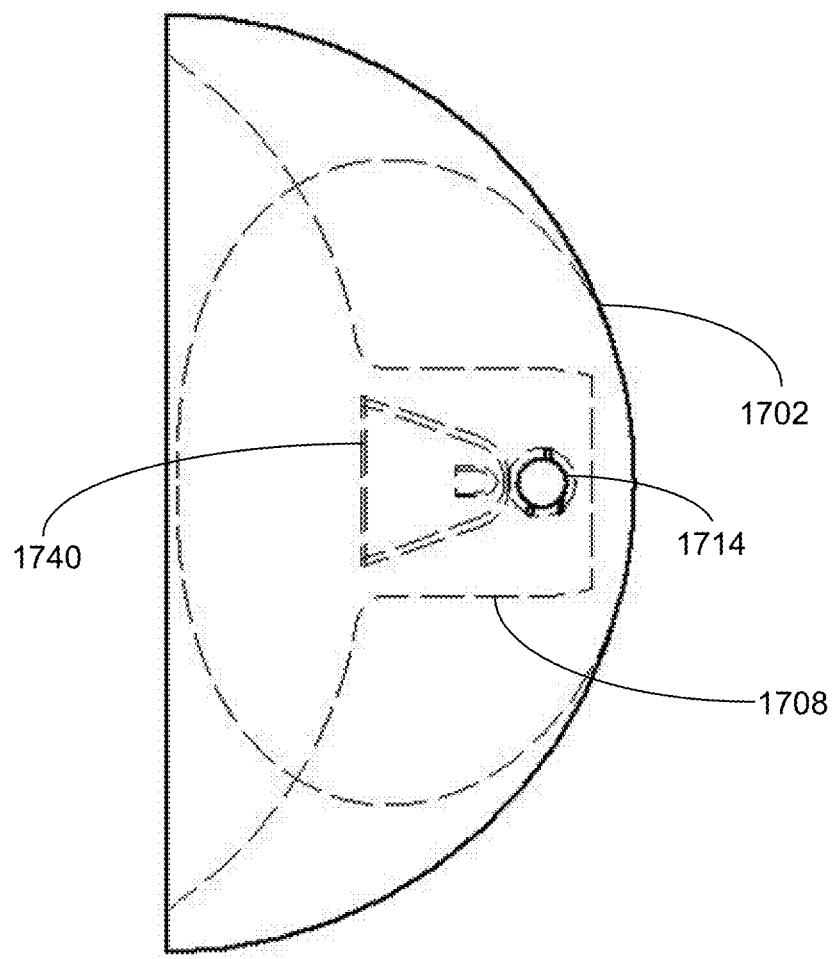
FIG. 17F depicts an inferior perspective view of a breast shield according to at least one embodiment described herein.
Figure 18B:
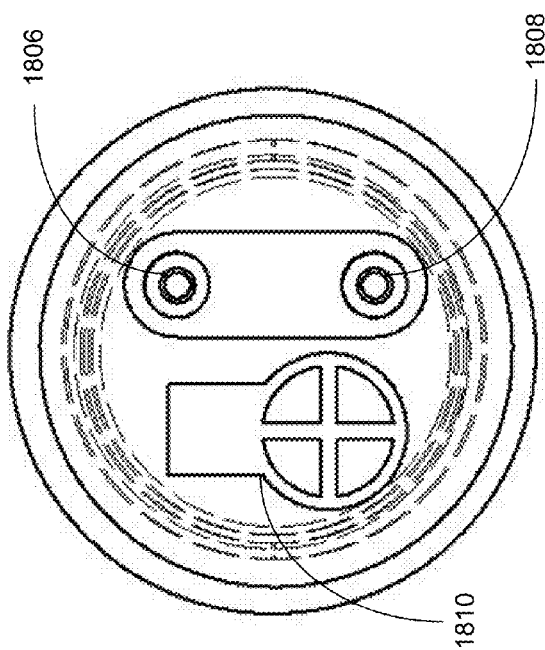
FIG. 18B depicts a top perspective view of a collection container according to at least one embodiment described herein.
Figure 18A:
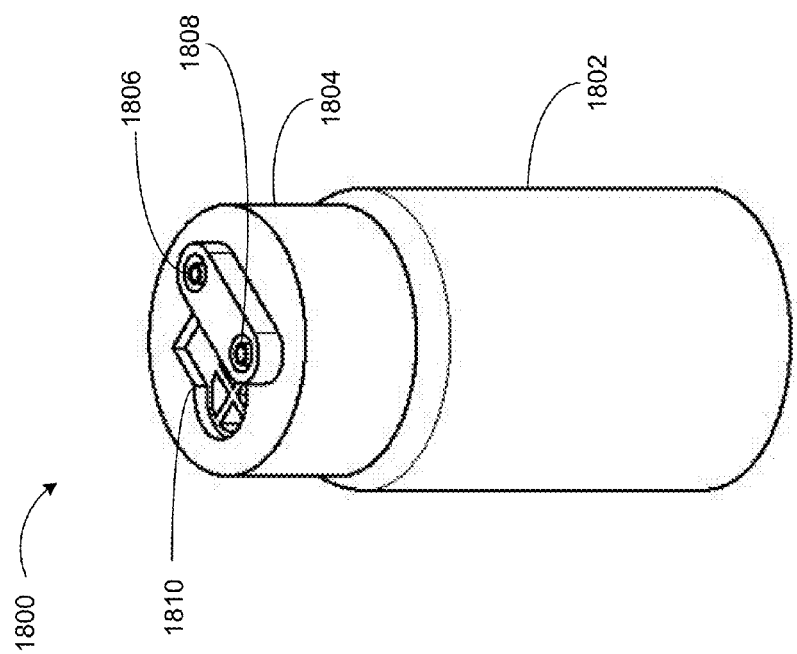
FIG. 18A depicts an oblique perspective view of a collection container according to at least one embodiment described herein.
Figure 18D:
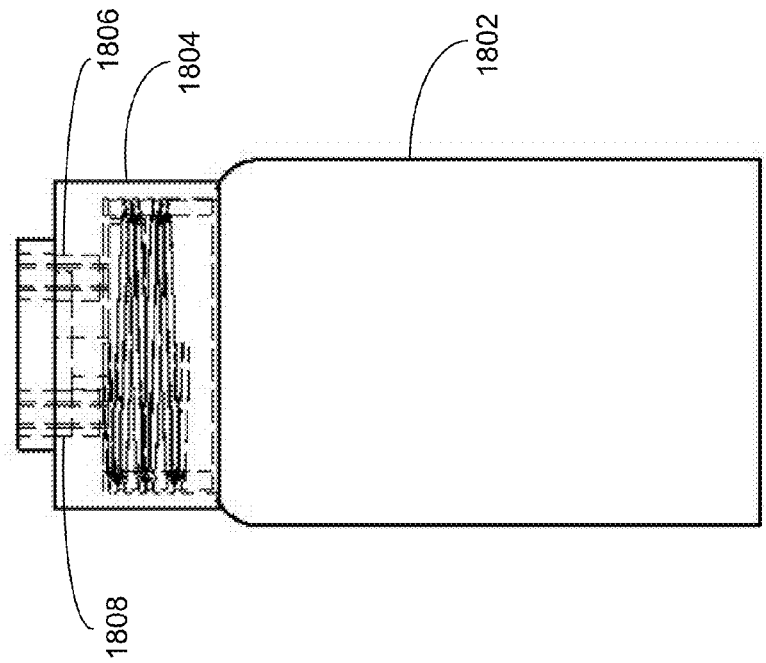
FIG. 18D depicts a side perspective view of a collection container according to at least one embodiment described herein.
Figure 18C:
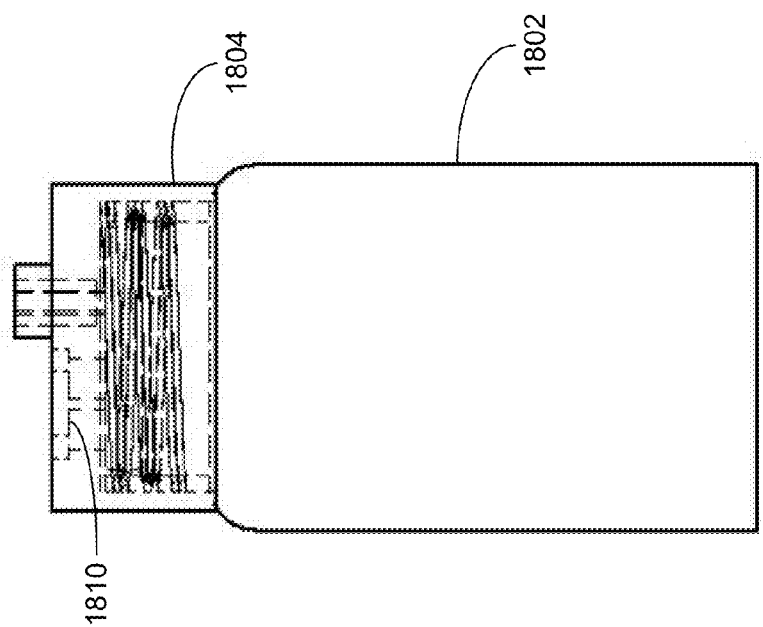
FIG. 18C depicts a side perspective view of a collection container according to at least one embodiment described herein.

In different embodiments, reservoir 10 may be different sizes. For example, reservoir 10 may be larger to accommodate more collection of milk, or smaller to prevent more collection of milk. In some embodiments, for example, reservoir 10 may be sized to fill a large portion of breast pump shield 200 between exterior portion 2 and interior portion 6. Alternatively, in order to prevent a large quantity of milk from being collected, some embodiments might not include reservoir 10 (e.g., a channel 12 may be directly connected to chamber 8). For example, FIG. 16C depicts a breast shield that has chamber 1608. Milk may collect at an end of chamber 1608 near channel 1612, and milk may be funneled into channel 1612.

In some embodiments, a valve may be included at or near an end of the chamber. For example, a one-way valve may be included that opens to allow milk to flow from the chamber to the reservoir and/or the channel (e.g., when suction is applied to the system). The one-way valve may close when suction is released. Thus, as cyclical pumping is performed, the valve may open and close in tandem with the pumping action. Specifically, the valve may open to allow for milk to flow from the nipple in the chamber to the reservoir and/or channel through the open valve when suction is applied by the pump, and the valve may close to prevent backflow from the channel and/or reservoir to the chamber when suction is not being applied by the pump.

According to at least one embodiment, breast pump shield 200 may include a channel 12. Channel 12 may extend from an end of chamber 8 and/or from reservoir 10 to an exterior of breast pump shield 200 (e.g., an outer surface of exterior portion 2). Channel 12 may be continuously surrounded and defined by a channel wall. In some embodiments, channel 12 may be the only path or opening from chamber 8 and/or reservoir 10 to the exterior surface of exterior portion 2. According to some aspects, suction from the pump may be applied to the breast through channel 12, and milk collected from the breast may exit breast pump shield 200 via channel 12.

In some embodiments, the collection tubing may be connected to a side portion of the breast shield. In some embodiments, the collection tubing may be connected to an inferior portion of the breast shield at or near a midline of the breast shield. In some embodiments, when breast pump shield 200 is attached to a breast, and a user of breast pump shield is upright in relation to the ground, channel 12 may extend from a lower-180° portion or lower-half (e.g., a portion of breast pump shield 200 that is closer to the ground than the nipple of the breast) of reservoir 10. In some embodiments, when the breast pump shield 200 is attached to a breast, and the user of breast pump shield 200 is sitting upright in relation to the ground, an end of channel 12 that is closer to reservoir 10 may be higher (e.g., further from the ground) than an end of channel 12 in communication with an outer surface of breast pump shield 200. In some embodiments, when breast pump shield 200 is attached to a breast, and a user of breast pump shield is upright in relation to the ground, channel 12 may extend to an exit point on a lower-180° portion or lower-half of breast pump shield 200 (e.g., a portion of breast pump shield 200 that is closer to the ground than an upper-180° portion or upper-half of breast pump shield 200). In some embodiments, suction applied by the pump through channel 12 may extract milk from the breast, and gravity may cause milk to flow from reservoir 10 through channel 12 toward an outside of breast pump shield 200. Alternatively, channel 12 may extend from any portion (e.g., a top half, a bottom half, a left half, a right half) of reservoir 10 toward an outside surface of breast pump shield 200, and suction applied by the pump through channel 12 may extract milk from the breast, and the suction may also cause milk to flow from reservoir 10 into channel 12 toward an outside of breast pump shield 200.

In some embodiments, channel 12 may be configured to receive a tubing (e.g., collection tubing). In some embodiments, a length of the channel 12 may receive the tubing (e.g., the tubing may be placed into channel 12 such that the tubing extends the length of channel 12 until the tubing is at or near reservoir 10. In some embodiments, a portion of the length of the channel 12 may receive the tubing.

In some embodiments, channel 12 may have diameter 36. In some embodiments, channel 12 may have a same diameter at an end closer to reservoir 10 as a diameter at an end closer to end 14. In some embodiments, channel 12 may have a smaller diameter at an end closer to reservoir 10 and a larger diameter at an end closer to end 14. Alternatively, in some embodiments, channel 12 may have a larger diameter at an end closer to reservoir 10 and a smaller diameter at an end closer to end 14.

In some embodiments, breast pump shield 200 may include an end 14 of channel 12. A tubing may be attached to channel 12 at end 14. In some embodiments, end 14 may attach to a connector (e.g., connector 160), which may allow for tubing of a particular size or range of sizes to be used with breast pump shield 200. In some embodiments, end 14 may provide a female connection for tubing or a connector. In some embodiments, end 14 may protrude from exterior portion 2 to provide a male connection for tubing or a connector. In some embodiments, end 14 may be retractable, such that end 14 may retract into breast pump shield 200, so as to not protrude beyond a surface of exterior portion 2 surrounding end 14 when end 14 is not connected to tubing or a connector.

In some embodiments, as depicted in FIGS. 16A-16E and 17A-17F, a breast shield may include a threaded channel (e.g., channel 1612, 1712). A threaded channel may receive a threaded end of a connector, which may allow for a more secure fit of a connector into the breast shield (e.g., at end 1614 or end 1714). A connector may be threaded on one end (e.g., an end that interfaces with breast shield at end 1614 or end 1714). A different (e.g., opposite) end of the connector may be configured to receive tubing. In some embodiments, the different end of the connector may non-removably receive tubing. For example, the end of the connector configured to interface with the tubing may provide an extremely tight fit with the tubing, such that once the connector is placed onto the tubing, the tubing cannot be removed. Different connectors may have different size ends to interface with different size tubing (e.g., for different pump systems). Alternatively or additionally, the end of the connector and/or tubing may include adhesive. Alternatively or additionally, the end of the connector may be a heat-shrink fit, such that after the tubing is inserted, a user may apply heat to the end of the connector to shrink the end of the connector around the tubing, to cause a tight (e.g., non-removable) connection with the tubing. Providing a tight connection with the tubing and/or a threaded connection with the breast shield may improve a vacuum or suction created through the tubing and/or connector to the shield.

Returning to FIG. 2, and as discussed above in connection with FIG. 1, channel 12 may be attached to a tubing that extends from breast pump shield 200 to a collection container for receiving breast milk. Channel 12 may be configured such that when breast pump shield 200 is attached to a breast, milk flows from the nipple in chamber 8, through reservoir 10 to channel 12, and through channel 12 to the tubing. As discussed above, the tubing may be attached to the channel 12 directly, or via a connector (e.g., connector 160). As discussed in connection with FIG. 1, milk may flow through the tubing to the collection container.

As mentioned above, FIGS. 16A-16E depict different views of an embodiment of a breast pump shield (e.g., breast pump shield 1600) that may be and/or have features similar to breast pump shield 200. For example, breast pump shield 1600 may include a concave interior surface (e.g., interior portion 1606), a convex exterior surface (e.g., exterior portion 1602), and a connecting surface (e.g., middle portion 1604) that connects the concave interior surface with the convex exterior surface. Breast pump shield 1600 may include a chamber (e.g., chamber 1608). Breast pump shield 1600 may include a channel (e.g., channel 1612) from the chamber to an exterior portion of the breast shield (e.g., at end 1614).

As mentioned above, FIGS. 17A-17F depict different views of an embodiment of a breast pump shield (e.g., breast pump shield 1700) that may be and/or have features similar to breast pump shield 200. For example, breast pump shield 1700 may include a concave interior surface (e.g., interior portion 1706), a convex exterior surface (e.g., exterior portion 1702), and a connecting surface (e.g., middle portion 1704) that connects the concave interior surface with the convex exterior surface. Breast pump shield 1700 may include a chamber (e.g., chamber 1708). Breast pump shield 1700 may include a channel (e.g., channel 1712) from the chamber to an exterior portion of the breast shield (e.g., at end 1714). As discussed above, breast shield 1700 may include an insert (e.g., insert 1740) in chamber 1708 between interior portion 1706 and an opening of channel 1712 into chamber 1708.

Figure 8:
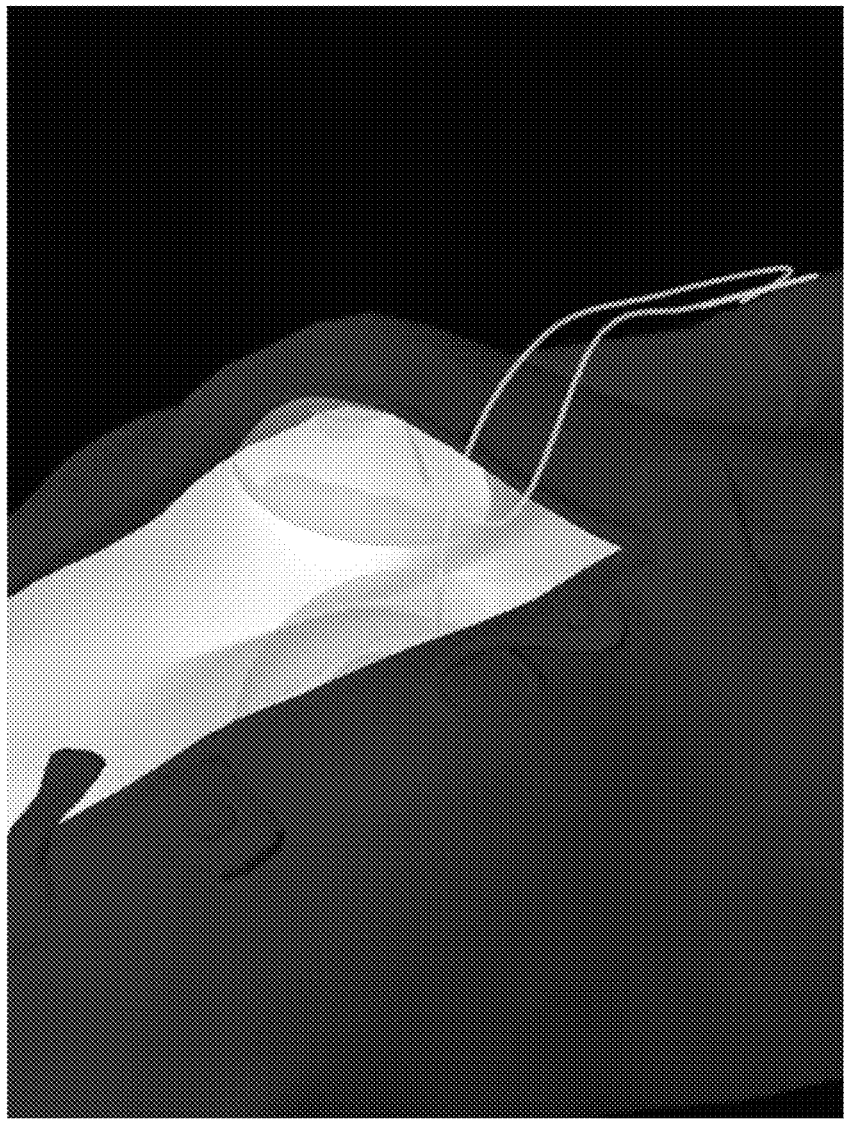
FIG. 8 is a perspective view of a woman utilizing two breast shields having tubing attached thereto according to at least one embodiment described herein.

FIG. 8 depicts a perspective view of an illustration of a woman utilizing two breast shields having tubing attached thereto, according to at least one embodiment described herein.

As shown in FIG. 8, the breast shield may be worn under a shirt or other clothing of a woman, which may make pumping breast milk more convenient, discreet, and efficient. For example, for a new mother who has many demands on her time, the breast shield described herein allows for more convenient pumping.

With previous systems, for example, a nursing woman would every few hours need to stop what she's doing, find a bathroom or other private place, pump milk, find a safe way to store the milk, and then return to whatever she was doing before. In a few hours, she would need to repeat the process.

With the present system, however, a woman who is engaged in a task (e.g., working at a desk) may simply insert the shield through the sleeve or collar of her shirt. The tubing may, in some embodiments, may be fed through the collar of a shirt. Alternatively or additionally, the tubing may be fed out of the bottom of a shirt, through the sleeve, or the bottom of a dress or skirt. The pump and/or collection container may be placed on a desk or other surface directly, or may be discreetly placed in a purse, bag, satchel, or other container on a desk or other surface, which may allow the woman to continue performing the task in which she was previously engaged with minimal interruption, and without attracting the attention of those around her. After the pumping is complete, the woman may simply remove the shield or shields the same way the shield or shields were inserted (e.g., through a sleeve or collar). In some embodiments, the shield and/or tubing may be cleaned for later reuse. In some embodiments, the shield and/or tubing may be disposable. Thus, the woman may simply dispose of the shield and tubing after she is finished pumping. Thus, the system provides for a more convenient and efficient solution for pumping breast milk.

Furthermore, in contrast to other breast pump systems, the breast pump device or system described herein may include far fewer devices. For example, a breast shield may be a single piece connected by a single tube to a collection container, which may be connected by a single tube to a pump. By having fewer pieces, the system may more easily be assembled, disassembled, cleaned, and the like.

Figure 9:
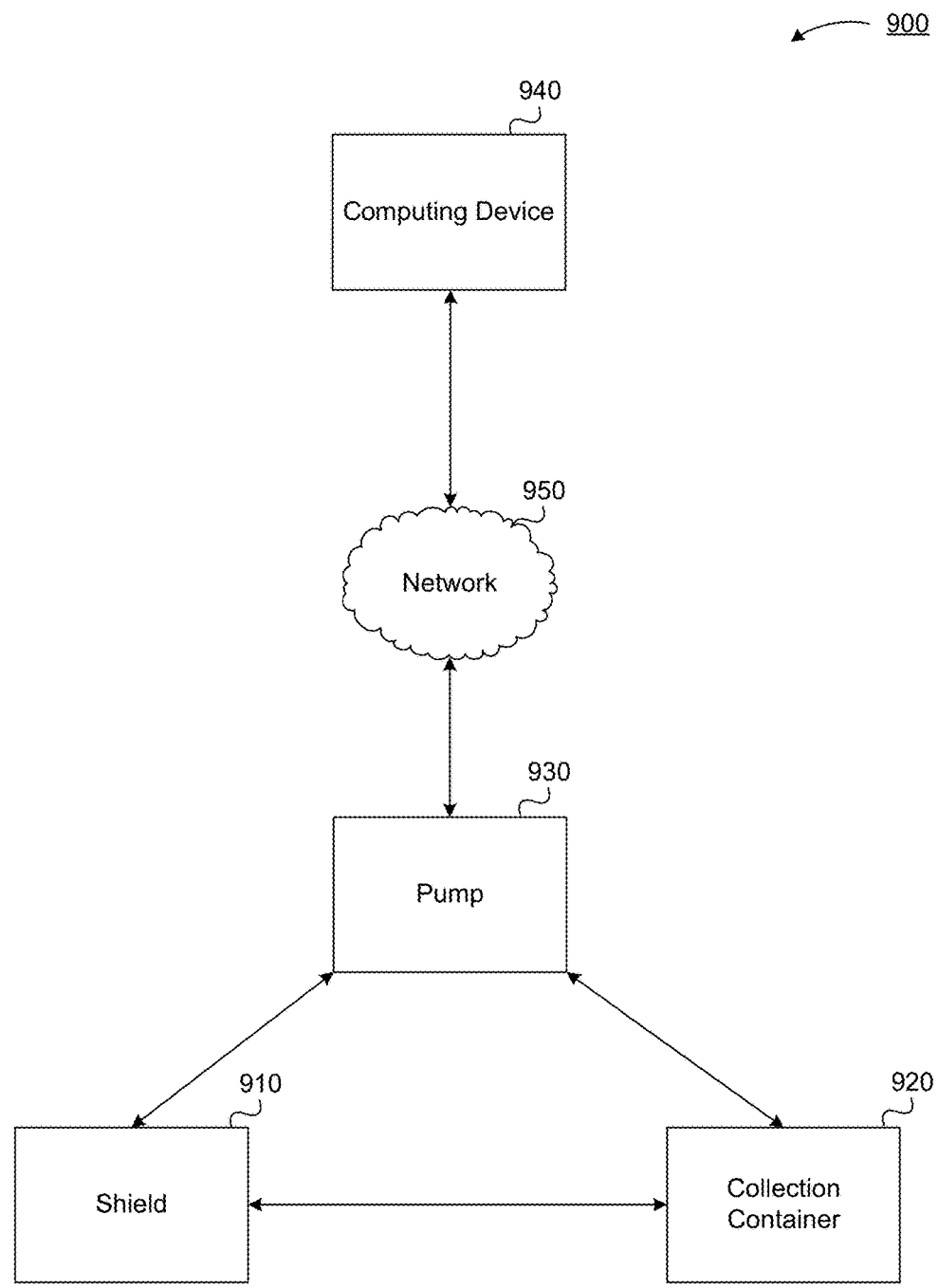
FIG. 9 depicts an illustrative computing environment according to at least one embodiment described herein.

FIG. 9 depicts an illustrative block diagram of a computing environment in accordance with some features described herein. It is noted that various connections between elements are discussed in the following description. It is noted that these connections are general and, unless specified otherwise, may be direct or indirect, wired or wireless, and that the specification is not intended to be limiting in this respect.

A computing environment (e.g., computing environment 900) may include a breast shield (e.g., shield 910), a collection container (e.g., collection container 920), and a pump (e.g., pump 930). As described previously, the breast shield, the collection container, and the pump may be physically connected using tubing (not depicted). The computing environment may include one or more computing devices (e.g., computing device 940).

One or more of the breast shield (e.g., shield 910), the collection container (e.g., collection container 920), and the pump (e.g., pump 930) may include one or more electrical components that may send data signals between each other and/or a computing device (e.g., 940).

Computing device 940 may be configured to be used by a user (e.g., a nursing mother or lactating woman) of a breast pump device or system (e.g., pump 930, shield 910, and collection container 920). Computing device may be used by a spouse or other family member of the user, a health-care worker (e.g., a doctor, nurse, aide, or the like), a caretaker, a nanny, a friend, or the like.

In one or more arrangements, computing device 940 may be any type of computing device capable of receiving a user interface, receiving input via the user interface, and communicating the received input to one or more other computing devices. For example, computing device 940 may, in some instances, be and/or include server computers, desktop computers, laptop computers, tablet computers, smart phones, personal digital assistants, pagers, or the like. Any and/or all of shield 910, collection container 920, pump 930, and/or computing device 940 may, in some instances, be or include special-purpose computing devices configured to perform specific functions.

Computing environment 900 also may include one or more networks, which may interconnect one or more of shield 910, collection container 920, pump 930, and computing device 940. For example, computing environment 100 may include network 950, as depicted in FIG. 9. Network 950 may include one or more sub-networks (e.g., local area networks (LANs), wide area networks (WANs), or the like). Network 950 may be associated with a particular organization (e.g., a corporation, educational institution, governmental institution, or the like) and may interconnect one or more computing devices associated with the organization. Network 950 may be a home network, an ad-hoc network, a ring network, or another type of network.

Figure 10:
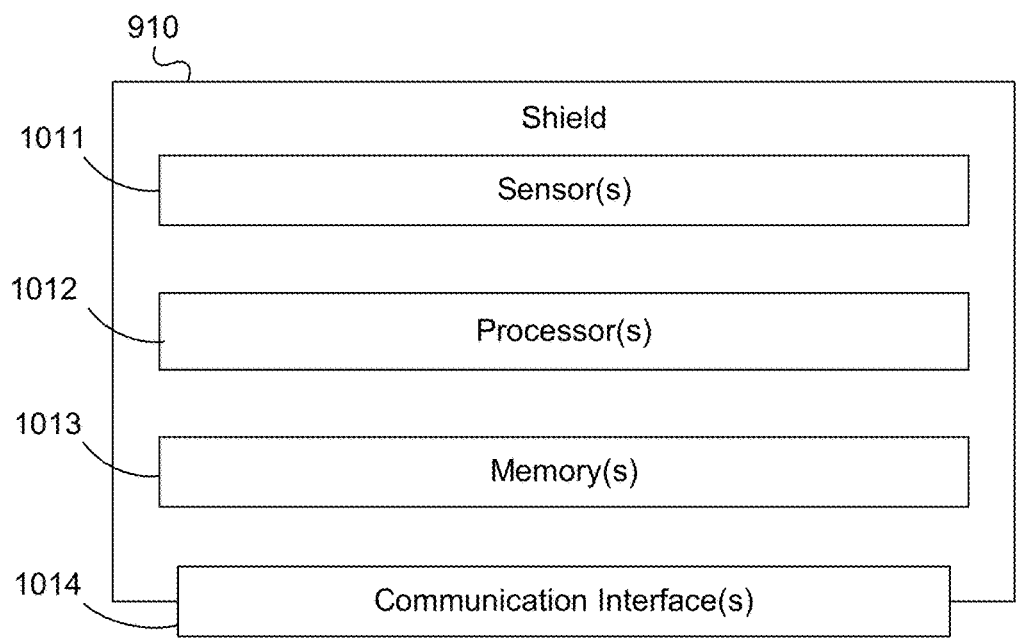
FIGS. 10-12 depict illustrative block diagrams of various components of a breast pump device according to at least one embodiment described herein.

FIG. 10 illustrates shield 910, which may include one or more sensor(s) 1011, processor(s) 1012, memory(s) 1013, and communication interface(s) 1014. A data bus may interconnect sensor(s) 1011, processor(s) 1012, memory(s) 1013, and communication interface(s) 1014. Communication interface(s) 1014 may be a network interface configured to support communication between shield 910 and one or more devices and/or networks (e.g., collection container 920, pump 930, computing device 940, network 950, or the like). Communication with other devices via communication interface(s) 1014 may be direct (e.g., using BLUETOOTH, near-field communication (NFC), WIFI, AIRDROP, or the like) or indirect (e.g., via one or more other devices, such as devices in network 950).

Sensor(s) 1011 may include one or more sensors that may be used to provide data that may assist a user of shield 910 in more efficient use of a breast pump device or system. For example, sensor(s) 1011 may include a temperature sensor. A temperature sensor may be configured to sense a temperature of milk that is coming out of a nipple and through shield 910. For example, a temperature sensor may be placed in one or more of chamber 8, reservoir 10, channel 12, and end 14. In another example, sensor(s) 1011 may include a flow sensor or flow measuring device. For example, a flow sensor or flow measuring device may be placed in one or more of chamber 8, reservoir 10, channel 12, and end 14. The flow sensor or flow measuring device may determine a volume of milk that is flowing through the shield over a period of time, and thereby allow for an accurate method for measuring a volume of milk being produced. In another example, sensor(s) 1011 may include a heart-rate monitor, which may measure a heart rate of a woman as she is using the breast pump device or system. For example, the heart-rate monitor may be integrated into or near interior portion 6 and/or middle portion 4 of a shield (e.g., shield 910), such that the heart-rate monitor is positioned over or near a heart of the woman using shield 910.

Memory(s) 1013 may include a hard drive, solid state drive, flash memory, random-access memory (RAM), read-only memory (ROM), removable storage, NFC tag, radio-frequency identification (RFID) tag, or the like. Memory(s) 1013 may include one or more program modules having instructions that, when executed by processor(s) 1012, cause shield 910 to perform one or more functions described herein and/or one or more databases that may store and/or otherwise maintain information that may be used by such program modules and/or processor(s) 1012. In some instances, the one or more program modules may be stored by and/or maintained in different memory units of shield 910 and/or by different devices that may form and/or that are connected to or in communication with shield 910. For example, the instructions may cause shield 910 to perform one or more of activating, deactivating, sending instructions to, and receiving data from one or more of sensor(s) 1011. The instructions may further cause shield 910 to process data received from sensor(s) 1011, and/or data stored in memory(s) 1013. The instructions may further cause shield 910 to receive data from or transmit data to another device (e.g., collection container 920, pump 930, computing device 940, network 950, or the like), for example via one or more of near-field communication radio(s) 1014 and/or communication interface(s) 1015. In some examples, memory(s) 1013 may include an NFC tag that may include an identifier (e.g., an identification number) of shield 910.

Figure 11:
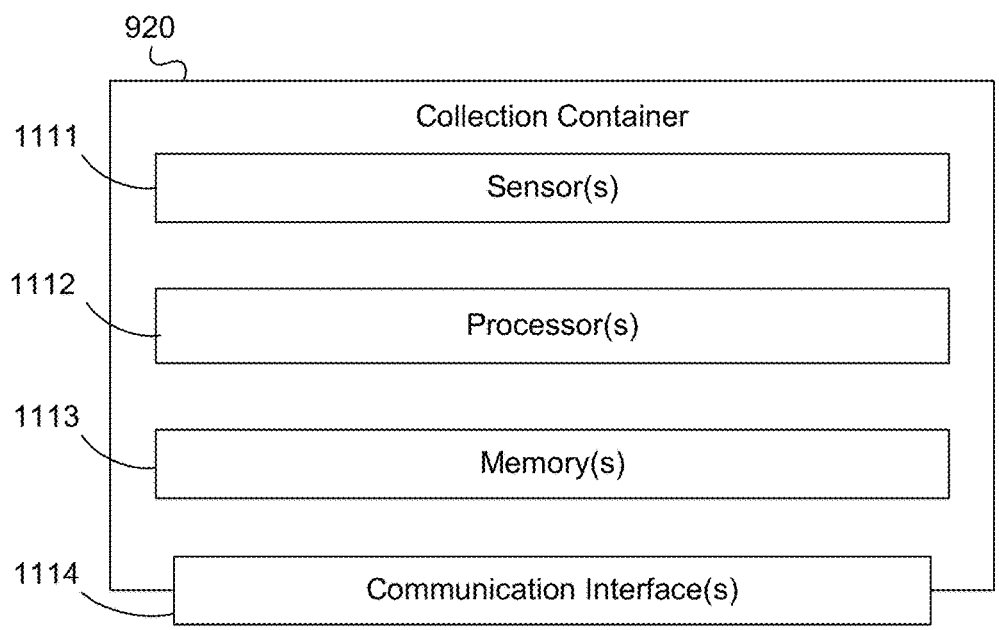

FIG. 11 illustrates collection container 920, which may include one or more sensor(s) 1111, processor(s) 1112, memory(s) 1113, and communication interface(s) 1114. A data bus may interconnect sensor(s) 1111, processor(s) 1112, memory(s) 1113, and communication interface(s) 1114. Communication interface(s) 1114 may be a network interface configured to support communication between collection container 920 and one or more devices and/or networks (e.g., shield 910, pump 930, computing device 940, network 950, or the like). Communication with other devices via communication interface(s) 1114 may be direct (e.g., using BLUETOOTH, near-field communication (NFC), WIFI, AIRDROP, or the like) or indirect (e.g., via one or more other devices, such as devices in network 950).

Sensor(s) 1111 may include one or more sensors that may be used to provide data that may assist a user of collection container 920 in more efficient use of a breast pump device or system.

For example, sensor(s) 1111 may include a temperature sensor. A temperature sensor may be configured to sense a temperature of milk that is coming into collection container 920. For example, a temperature sensor may be placed in a portion of collection container 920 where milk is coming in (e.g., near a point where tubing enters collection container 920), and/or a temperature sensor may be placed in a portion of collection container 920 where milk is stored (e.g., if collection container 920 is a bottle, a temperature sensor may be on, in, or near a wall or bottom of the bottle).

In another example, sensor(s) 1111 may include a flow sensor or flow measuring device. For example, a flow sensor or flow measuring device may be placed in a portion of collection container 920 where milk is coming in (e.g., near a point where tubing enters collection container 920), and measure a volume of milk that enters collection container 920. In another example, sensor(s) 1111 may include a fill sensor, which may sense when collection container 920 is getting full. For example, the fill sensor may be placed near the top of collection container 920, and sense how much milk is in collection container 920 relative to an amount of available storage space in collection container 920.

In another example, sensor(s) 1111 may include one or more sensors to determine properties of milk within or entering collection container. For example, a sensor may determine a caloric count of the milk. In another example, a sensor may determine a fat content of the milk.

Memory(s) 1113 may include a hard drive, solid state drive, flash memory, random-access memory (RAM), read-only memory (ROM), removable storage, NFC tag, or the like. Memory(s) 1113 may include one or more program modules having instructions that, when executed by processor(s) 1112, cause collection container 920 to perform one or more functions described herein and/or one or more databases that may store and/or otherwise maintain information that may be used by such program modules and/or processor(s) 1112. In some instances, the one or more program modules may be stored by and/or maintained in different memory units of shield 910 and/or by different devices that may form and/or that are connected to or in communication with collection container 920. For example, the instructions may cause collection container 920 to perform one or more of activating, deactivating, sending instructions to, and receiving data from one or more of sensor(s) 1111. The instructions may further cause collection container 920 to process data received from sensor(s) 1111, and/or data stored in memory(s) 1113. The instructions may further cause collection container 920 to receive data from or transmit data to another device (e.g., shield 910, pump 930, computing device 940, network 950, or the like), for example via one or more of near-field communication radio(s) 1114 and/or communication interface(s) 1115. In some examples, memory(s) 1113 may include an NFC tag that may include an identifier (e.g., an identification number) of collection container 920.

Figure 12:
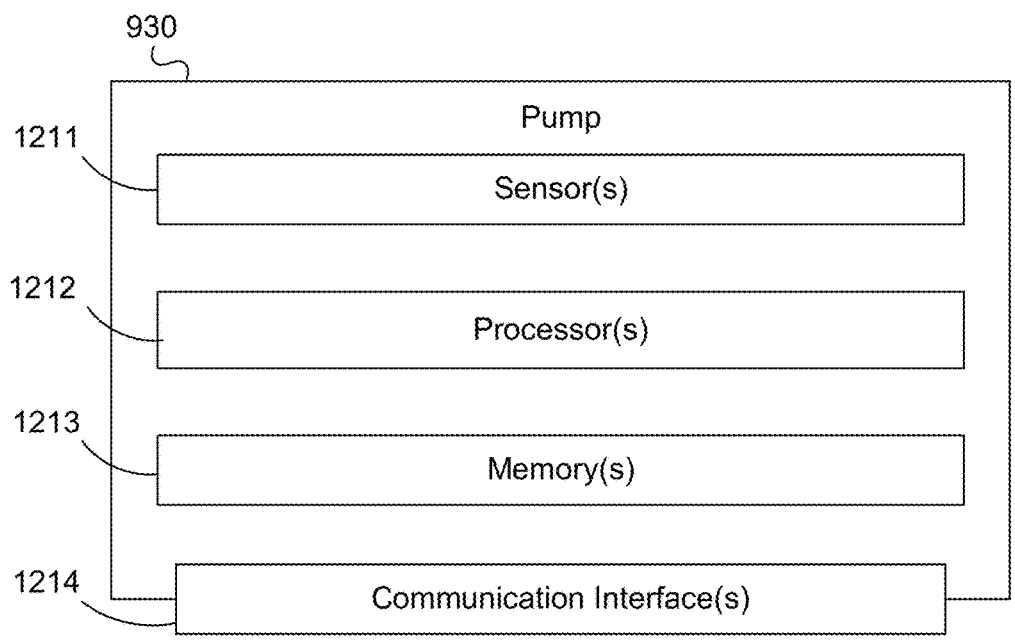

FIG. 12 illustrates pump 930, which may include one or more sensor(s) 1211, processor(s) 1212, memory(s) 1213, and communication interface(s) 1214. A data bus may interconnect sensor(s) 1211, processor(s) 1212, memory(s) 1213, and communication interface(s) 1214. Communication interface(s) 1214 may be a network interface configured to support communication between pump 930 and one or more devices and/or networks (e.g., shield 910, collection container 920, computing device 940, network 950, or the like). Communication with other devices via communication interface(s) 1214 may be direct (e.g., using BLUETOOTH, near-field communication (NFC), WIFI, AIRDROP, or the like) or indirect (e.g., via one or more other devices, such as devices in network 950).

Sensor(s) 1211 may include one or more sensors that may be used to provide data that may assist a user of pump 930 in more efficient use of a breast pump device or system. For example, sensor(s) 1211 may include a temperature sensor. A temperature sensor may be configured to sense a temperature of pump 930 to avoid overheating. In another example, sensor(s) 1211 may include a pressure gauge and/or vacuum sensor. For example, a pressure gauge and/or vacuum sensor may sense an amount of pressure within the breast pump device or system (e.g., from pump 930, through pump tubing, in collection container 920, through collection tubing, and in shield 910), which may be used to determine how much vacuum exists and/or an amount of suction that exists. Thereby, a metric for measuring effectiveness and/or proper functioning of a breast pump device may be measured. In another example, sensor(s) 1211 may include an airflow sensor, which may detect an amount of air moving through the breast pump system, to determine a volume of air and/or liquid that is being moved with each pump.

Memory(s) 1213 may include a hard drive, solid state drive, flash memory, random-access memory (RAM), read-only memory (ROM), removable storage, NFC tag, or the like. Memory(s) 1213 may include one or more program modules having instructions that, when executed by processor(s) 1212, cause pump 930 to perform one or more functions described herein and/or one or more databases that may store and/or otherwise maintain information that may be used by such program modules and/or processor(s) 1212. In some instances, the one or more program modules may be stored by and/or maintained in different memory units of pump 930 and/or by different devices that may form and/or that are connected to or in communication with pump 930. For example, the instructions may cause pump 930 to perform one or more of activating, deactivating, sending instructions to, and receiving data from one or more of sensor(s) 1211. The instructions may further cause pump 930 to process data received from sensor(s) 1211, and/or data stored in memory(s) 1213. The instructions may further cause pump 930 to receive data from or transmit data to another device (e.g., shield 910, collection container 920, computing device 940, network 950, or the like), for example via one or more of near-field communication radio(s) 1214 and/or communication interface(s) 1215. In some examples, memory(s) 1213 may include an NFC tag that may include an identifier (e.g., an identification number) of pump 930.

Figure 13:
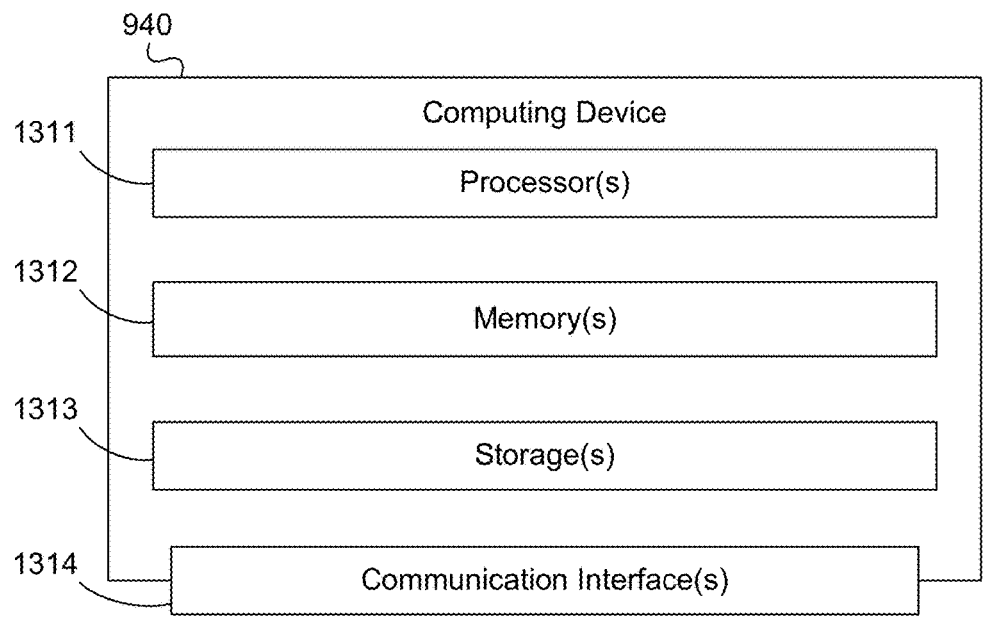
FIG. 13 is an illustrative block diagram of a computing device according to at least one embodiment described herein.

FIG. 13 illustrates computing device 940, which may include one or more processor(s) 1311, memory(s) 1312, storage(s) 1313, and communication interface(s) 1314. A data bus may interconnect processor(s) 1311, memory(s) 1312, storage(s) 1313, and communication interface(s) 1314. Communication interface(s) 1314 may be a network interface configured to support communication between computing device 940 and one or more devices and/or networks (e.g., shield 910, collection container 920, pump 930, network 950, or the like). Communication with other devices via communication interface(s) 1314 may be direct (e.g., using BLUETOOTH, near-field communication (NFC), WIFI, AIRDROP, or the like) or indirect (e.g., via one or more other devices, such as devices in network 950).

Memory(s) 1312 may include a hard drive, solid state drive, flash memory, random-access memory (RAM), read-only memory (ROM), removable storage, NFC tag, or the like. Memory(s) 1312 may include one or more program modules having instructions that, when executed by processor(s) 1311, cause computing device 940 to perform one or more functions described herein and/or one or more databases that may store and/or otherwise maintain information that may be used by such program modules and/or processor(s) 1311. In some instances, the one or more program modules may be stored by and/or maintained in different memory units of computing device 940 and/or by different devices that may form and/or that are connected to or in communication with computing device 940. For example, the instructions may include instructions that cause computing device 940 to execute a computer-executable application that receives, processes, and stores data received from one or more of shield 910, collection container 920, and pump 930. The computer-executable application may include features that include tracking an amount of milk produced in each pumping session, tracking an amount of milk currently available, tracking when each portion of milk is pumped and/or consumed, determining and/or providing alerts regarding a pumping schedule to maintain healthy milk production and/or sufficient milk for feeding a baby, tracking temperature of milk throughout the pumping and storage process, tracking a number of uses of a shield, a collection container, and a pump, and the like.

Figure 14:
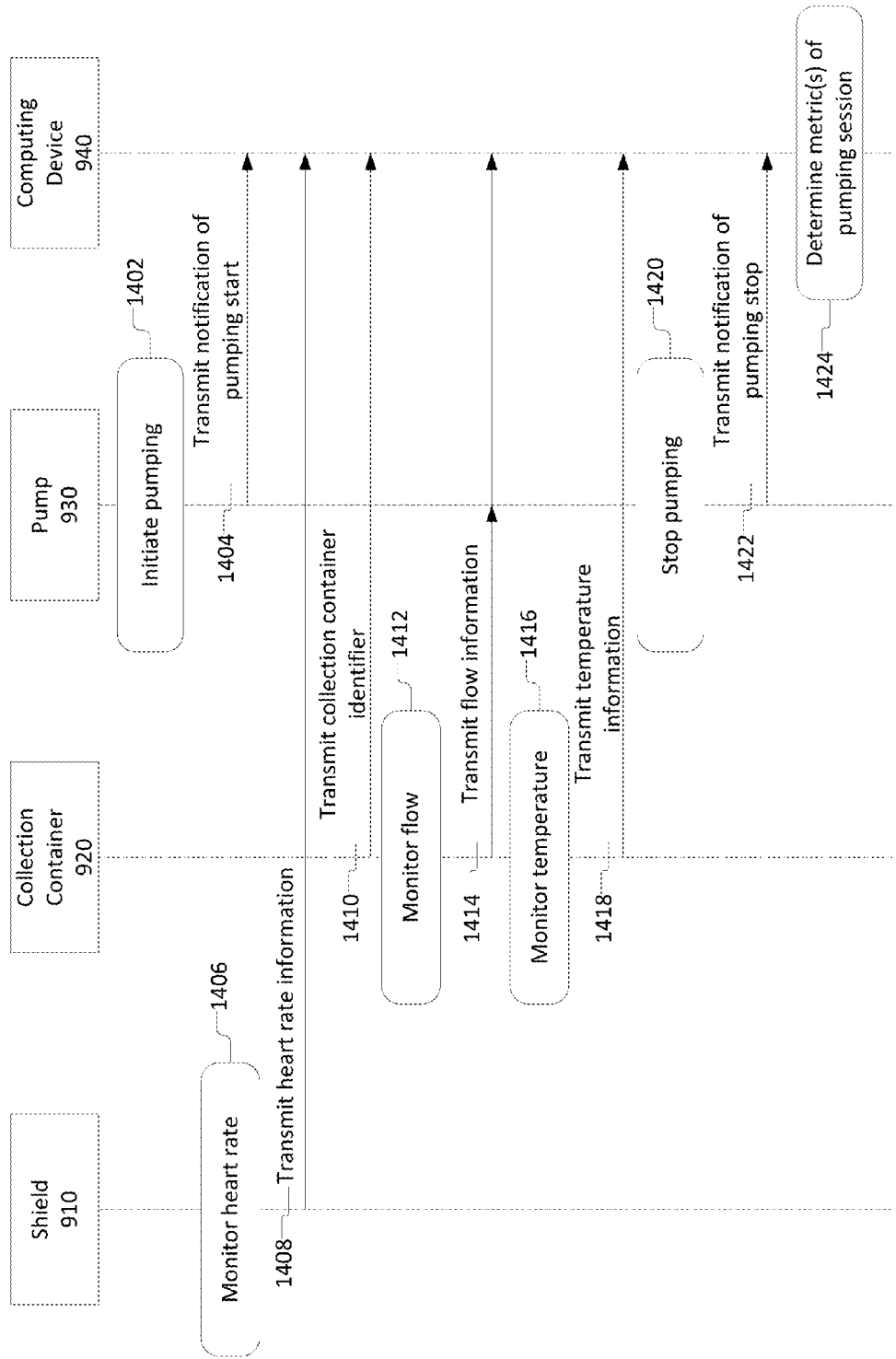
FIG. 14 is an illustrative flow diagram according to at least one embodiment described herein.

FIG. 14 depicts an illustrative flow for one or more features of a breast pump device or system. As depicted in FIG. 14, shield 910, collection container 920, pump 930, and computing device 940 may be in communication. One or more of the steps described may be performed in parallel with another step. One or more of the steps may be performed in any order, and/or repeated any number of times.

In step 1402, the pump may initiate pumping. For example, the user may press a switch to activate the pump. In some embodiments, the computing device may transmit a signal to the pump to activate the pump.

In step 1404, the pump may transmit to the computing device a notification that the pump started pumping. The computing device may associate a timestamp with a time of the notification that the pump started pumping.

In step 1406, the shield may monitor a heart rate of a wearer of the shield. In step 1408, the shield may transmit the heart rate of the wearer of the shield to the computing device.

In step 1410, the collection container may transmit an identifier of the collection container to the computing device. For example, the identifier may include an RFID identifier of the collection container. The collection container identifier may be a string or number that is unique to the collection container.

In step 1412, the collection container may monitor flow of breast milk into the collection container. In some embodiments, the shield may alternatively or additionally monitor flow of breast milk through one or more parts of the shield.

In step 1414, the collection container may transmit flow information to the computing device. In some embodiments, the shield may alternatively or additionally transmit flow information to the computing device. In some embodiments, the collection container and/or the shield may transmit flow information to the pump.

In step 1416, the collection container may monitor a temperature of breast milk in the collection container. Alternatively or additionally, the collection container may monitor an interior temperature of the collection container. Alternatively or additionally, the collection container may monitor an ambient temperature of a location where the collection container is located. In step 1418, the collection container may transmit temperature information to the computing device.

In some instances, the milk coming out of the breast will be safe, regardless of the temperature at which the milk comes out of the breast. But depending on the temperature of the milk when the comes out of the breast, as well as the temperature at which the milk is maintained after the milk comes out of the breast, may be used to determine how long of a period of time for which the milk may be maintained at a particular temperature, when the milk needs to be refrigerated, when the milk needs to be used, and/or when the milk is no longer usable.

In step 1420, the pump may stop pumping. For example, the user may press a switch to stop the pump. In some embodiments, the computing device may transmit a signal to the pump to stop the pump.

In some embodiments, the pump and/or the computing device may determine, based on the flow information (e.g., in the flow information transmitted in step 1414), that a flow rate of the breast milk is dropping below a threshold flow rate. Once the flow rate drops below the threshold flow rate, the pump may be stopped. For example, the computing device may send a signal to the pump to stop the pump. Alternatively, the pump may determine, based on the flow rate, that the pump should be stopped, and stop the pump.

In step 1422, the pump may transmit to the computing device a notification that the pump stopped pumping. The computing device may associate a timestamp with a time of the notification that the pump stopped pumping.

In step 1424, the computing device may determine one or more metrics of the pumping session.

For example, based on communication with one or more of the shield, the collection container, and the pump, a computer-executable application on the computing device may allow a user to track when she begins pumping, when the milk begins to flow, how much milk she has pumped, how long she pumped for, when she is starting to slow down, and the like.

The computer-executable application may track a time when milk was pumped. The time of the pumping may be associated with an identifier (e.g., an RFID tag) of a collection container that was used for collecting milk at a particular time.

The computer-executable application may track an available milk supply. For example, the application could track whether a milk supply is increasing or decreasing over time, whether sufficient milk is being produced to feed a baby drinking the milk, optimal pumping and/or feeding times, and the like. In some embodiments, milk production data could be reviewed in conjunction with other record keeping apps/devices, which may track information such as diet, volume of water taken in, etc., to help a lactating woman understand the various factors that may alter her milk supply.

The computer-executable application may perform additional functions based on information gathered by sensors or other electrical hardware or software in one or more of the shield, the collection container, and the pump.

Figures 15A, 15B:
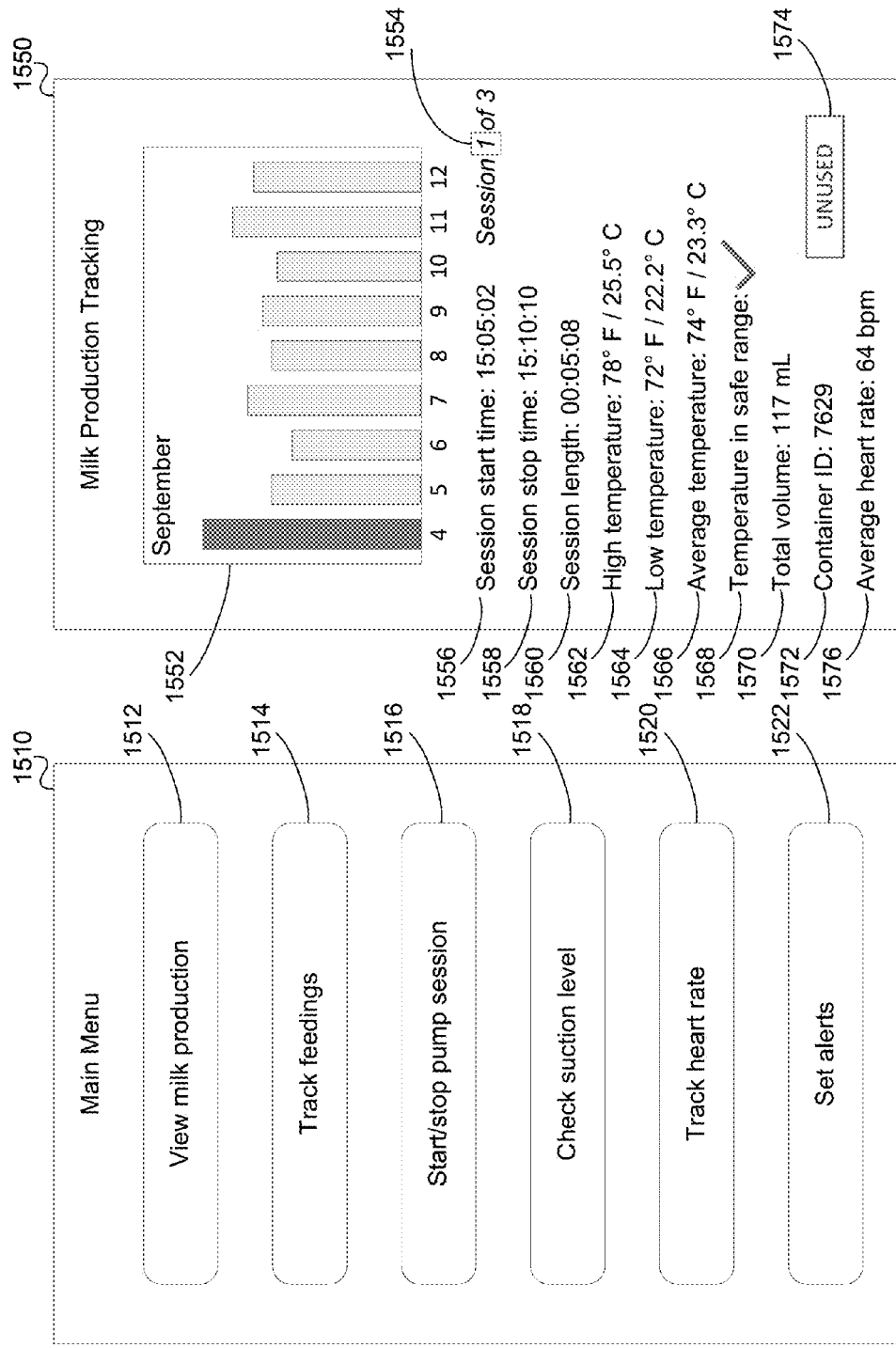
FIGS. 15A-15B depict illustrative graphical user interfaces of a computer-executable application according to at least one embodiment described herein.

FIGS. 15A-15B depict illustrative graphical user interfaces for a computer-executable application that may provide one or more features for use with a breast pump device or system.

For example, a mobile device of a user (e.g., computing device 940) may be configured to execute one or more computer-executable applications. The one or more computer-executable applications may be installed on a mobile device of the user. The one or more computer-executable applications may be downloaded to the mobile device from an public or private application store or catalog, may be directly installed onto the mobile device, and/or may be installed using a mobile device management system. The one or more computer-executable applications may work with all of the features described herein, or may work with a subset of the features.

FIG. 15A depicts an illustrative graphical user interface of one embodiment of a main screen 1510 of a computer-executable application that provides features related to a breast pump device or system. Main screen 1510 may include one or more options for actions that the device executing the computer-executable application may perform. One or more of the actions may be initiated by pressing a button on the graphical user interface (e.g., button 1512, button 1514, button 1516, button 1518, button 1520, button 1522).

Button 1512 may, when pressed, cause the computer-executable application to display a screen for viewing and/or tracking milk production. In some embodiments, the screen may be similar to screen 1550, depicted in FIG. 15B.

As shown in FIG. 15B, screen 1550 may include one or more graphical user interface elements for viewing information related to milk production of a lactating woman using a breast pump device or system.

Screen 1550 may include a graphical chart 1552, which may display a graphical view of a volume of milk produced each day in a period of time. Graphical chart 1552 may display a chart according to amount of milk produced each pumping session, each day, each of a number of days, each week, each month, each year, or according to another period of time.

Screen 1550 may also display one or more pieces of information regarding a pumping session. For example, if September 4 is selected (as indicated by the darker bar in graphical chart 1552), information for one or more of the pumping sessions on September 4 may be viewed. For example, selector 1554 may allow for selection of a particular pumping session on the day selected in graphical chart 1552. As illustrated, September 4 may have had three pumping sessions, and screen 1550 may be an illustrative example of pumping information that may be displayed in accordance with pumping session one.

Screen 1550 may display one or more of session start time 1556, session stop time 1558, and session length 1560, which may be calculated based on a difference between session start time and session stop time.

Screen 1550 may display one or more of high temperature 1562, low temperature 1564, and average temperature 1566. Screen 1550 may display an indication 1568 of whether the temperature over the course of the pumping session is within a safe range. Alternatively or additionally, indication 1568 may be an indication of whether or not the temperature of the milk in the collection container has ever not been in a safe range, in a period of time elapsed since the pumping session. For example, if milk was accidentally left out for too long without being refrigerated or frozen, the collection container may transmit the temperature information to the computing device, which may update, based on the temperature information, indicator 1568.

Screen 1550 may display total volume 1570. Total volume 1570 may correspond to a total volume of milk produced during a particular pumping session, which may be calculated based on the flow information gathered by one or more of the shield and the collection container. In some embodiments, a total volume of milk produced during a day may be added up to determine a height of a bar for the day on graphical chart 1552.

Screen 1550 may display an identifier 1572 of a collection container that was used for the pumping session for which information is displayed. For example, an RFID identifier of the collection container may be transmitted to the computing device before, during, or after a pumping session, and the computing device may associate the identifier of the collection container with the particular pumping session. Indicator 1574 may show whether the milk in the collection container has been used or not. In some embodiments, once the milk has been used, indicator 1574 may be changed to show that the milk has been used. In some embodiments, the user may update the application to indicate that the milk has been used, which may allow the container to be tracked in conjunction with another pumping session. In some embodiments, one or more sensors in the container may detect when milk is no longer in the collection container (e.g., the milk was used or transferred), and the collection container may automatically transmit a signal to the computing device to inform the computing device that the collection container may be used for another pumping session.

Screen 1550 may display an average heart rate of a woman over the duration of a pumping session. The average heart rate may allow the woman to determine whether she is relaxed, stressed, anxious, nervous, or the like. In some instances, a heart rate may correspond to a volume of milk produced. Therefore, tracking a heart rate while pumping, and determining a volume of milk produced while pumping, may allow a woman to determine an optimal activity, state of mind, time of day, or other factor(s) that may assist in achieving an optimal heart rate for optimal milk production.

In some embodiments, screen 1550 may display information for past pumping sessions. In some embodiments, screen 1550 may display information regarding a current, ongoing pumping session. Screen 1550 may update with new information as a pumping session continues, allowing a woman to track details about a pumping session in real-time or near-real-time as the pumping session is happening.

Returning to FIG. 1510, screen 1510 may include additional buttons that correspond to additional features of the application. For example, button 1514 may correspond to one or more features of the application that allow for a user to track feedings of a baby or babies. The feeding schedule could be combined with a pumping schedule to determine an optimal number of times to pump, as well as the optimal times of day to pump.

Button 1522 may correspond to a feature of an application that may allow for setting alerts (e.g., an alert to pump at an optimal time, an alert to feed the baby, an alert to use milk that may no longer be usable after a certain period of time, an alert that the temperature was not in a safe range during a pumping session, or the like). Alerts may be provided on the computing device, in the application, via short message service, email, BLUETOOTH, phone call, or the like.

Button 1516 may correspond to a feature of the application that may allow for starting and/or stopping a pumping session. The application may, in some embodiments, be used to remotely control a pump. For example, if the pump is a small device configured to be worn on a belt or other article of clothing near the woman's body, it may be inconvenient to find a start/stop switch on the pump. Thus, the application may provide a convenient remote control function for a pump.

Button 1518 may correspond to a feature of the application that may allow for a woman to check for proper fit and/or function of the breast pump device and/or system. For example, the application may trigger and/or receive information regarding an internal vacuum pressure created within the breast pump system by the pump when the shield is attached to the woman's breast. By checking the suction level, the application may assist the woman in determining whether the shield is achieving sufficient suction to result in optimal milk production. If optimal suction level is not being achieved, the application may assist the woman (e.g., via visual prompts) in determining whether the shield is properly sized (e.g., too large, too small), whether one of the tubes has a leak, whether the collection container is sealing properly, or the like.

Button 1520 may correspond to a feature of the application that may allow a woman to track her heart rate. For example, a woman may desire to track her heart rate, even while she is not engaged in a pumping session. In some embodiments, a shield may be designed for all-day wear. A woman wearing the shield may use the application to receive heart-rate information gathered by one or more sensors in the shield, which may be transmitted to the application.

One or more aspects of the disclosure may be embodied in computer-usable data or computer-executable instructions, such as in one or more program modules, executed by one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, application-specific integrated circuits (ASICs), field programmable gate arrays (FPGA), and the like. Particular data structures may be used to more effectively implement one or more aspects of the disclosure, and such data structures are contemplated to be within the scope of computer executable instructions and computer-usable data described herein.

Various aspects described herein may be embodied as a method, an apparatus, or as one or more computer-readable media storing computer-executable instructions. Accordingly, those aspects may take the form of an entirely hardware embodiment, an entirely software embodiment, an entirely firmware embodiment, or an embodiment combining software, hardware, and firmware aspects in any combination. In addition, various signals representing data or events as described herein may be transferred between a source and a destination in the form of light or electromagnetic waves traveling through signal-conducting media such as metal wires, optical fibers, or wireless transmission media (e.g., air or space). In general, the one or more computer-readable media may include one or more non-transitory computer-readable media.

As described herein, the various methods and acts may be operative across one or more computing servers and one or more networks. The functionality may be distributed in any manner, or may be located in a single computing device (e.g., a server, a client computer, and the like). For example, in alternative embodiments, one or more of the computing platforms discussed above may be combined into a single computing platform, and the various functions of each computing platform may be performed by the single computing platform. In such arrangements, any and/or all of the above-discussed communications between computing platforms may correspond to data being accessed, moved, modified, updated, and/or otherwise used by the single computing platform. Additionally or alternatively, one or more of the computing platforms discussed above may be implemented in one or more virtual machines that are provided by one or more physical computing devices. In such arrangements, the various functions of each computing platform may be performed by the one or more virtual machines, and any and/or all of the above-discussed communications between computing platforms may correspond to data being accessed, moved, modified, updated, and/or otherwise used by the one or more virtual machines.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, and one or more depicted steps may be optional in accordance with aspects of the disclosure.

What is claimed is:

1. A breast pump device comprising:
    a breast shield for receiving a human breast, the breast shield comprising:
        a curved convex exterior surface;
        a concave interior surface configured to contact the human breast;
        a chamber comprising a first end at an opening formed in the concave interior surface, wherein the chamber is configured such that a nipple is within the chamber when the breast shield is attached to the human breast;
        a reservoir in communication with a second end of the chamber opposite the first end of the chamber; and
        a channel between the reservoir and the curved convex exterior surface, the channel configured to receive a tubing, the channel extending from the reservoir to an exterior of the curved convex exterior surface, an entire length of the channel being defined by a channel wall,
        wherein the breast shield is formed of a single piece;
    a collection container for receiving breast milk, the collection container being separate from the breast shield;
    a flexible collection tubing connecting the breast shield to the collection container; and
    a pump connected to the collection container via pump tubing, the pump configured to create suction in the breast shield via the collection tubing, such that the suction draws the breast milk from the human breast, and the breast milk exits the breast shield into the collection container through the collection tubing.

2. The breast pump device of claim 1, wherein the collection tubing is connected to the breast shield via a side portion of the breast shield.

3. The breast pump device of claim 1, comprising:
a connector between the collection tubing and the breast shield, the connector being configured to receive one of a plurality of collection tubings of different respective diameters.

4. The breast pump device of claim 1, wherein the breast shield is made of silicone.

5. The breast pump device of claim 1, wherein the pump tubing connecting the pump to the collection container is shorter than the collection tubing connecting the breast shield to the collection container.

6. The breast pump device of claim 1, wherein the collection container is configured to be outside of a shirt of a user of the breast shield when the breast shield is attached to the human breast.

7. The breast pump device of claim 1, wherein the breast shield comprises:
a channel extending from an internal reservoir of the breast shield to an exterior surface of the breast shield, the channel being continuously surrounded by a channel wall from the internal reservoir of the breast shield to the exterior surface of the breast shield,
wherein the channel is an only opening between the internal reservoir of the breast shield and the exterior surface of the breast shield.

8. The breast pump device of claim 7, wherein the breast shield comprises:
a breast shield tubing extending along the channel, an end of the breast shield tubing connecting to the collection tubing,
wherein the breast shield tubing is configured to transmit its the suction to an interior portion of the breast shield such that the breast milk exits the breast shield through the breast shield tubing.

9. The breast pump device of claim 1, wherein a longest length of the breast shield is less than four times a thickness of the breast shield, the thickness of the breast shield being orthogonal to the longest length of the breast shield.

10. The breast pump device of claim 1, comprising:
a pressure gauge between a first portion of the pump tubing and a second portion of the pump tubing, the pressure gauge being configured to measure the suction created by the pump.

11. The breast pump device of claim 1, wherein a length of the collection tubing is at least twelve inches long between an exterior of the breast shield and the collection container.

12. The breast pump device of claim 1, wherein the breast shield does not directly contact the collection container.

13. The breast pump device of claim 1, wherein a thickness of the breast shield is less than a diameter of the breast shield, the thickness of the breast shield being orthogonal to the diameter of the breast shield.

14. The breast pump device of claim 1, wherein a length of the collection tubing is at least twelve inches long between an exterior of the breast shield and the collection container.

15. The breast pump device of claim 1, wherein a longest length of the breast shield is less than four times a thickness of the breast shield, the thickness of the breast shield being orthogonal to the longest length of the breast shield.

16. The breast pump device of claim 1, comprising a valve configured to allow one-way flow into the collection container.

17. The breast pump device of claim 1, wherein the pump is a manual pump.

18. The breast pump device of claim 1, wherein the pump is an electric pump.

19. A breast shield comprising:
a curved convex exterior surface;
a concave interior surface configured to contact a breast;
a chamber comprising a first end at an opening formed in the concave interior surface, wherein the chamber is configured such that a nipple is within the chamber when the breast shield is attached to the breast;
a reservoir in communication with a second end of the chamber opposite the first end of the chamber; and
a channel between the reservoir and the curved convex exterior surface, the channel configured to receive a tubing, the channel extending from the reservoir to an exterior of the curved convex exterior surface, an entire length of the channel being defined by a channel wall,
wherein the breast shield is formed of a single piece.

20. The breast shield of claim 19, comprising:
a channel extending from an internal reservoir of the breast shield to an exterior surface of the breast shield, the channel being continuously surrounded by a channel wall from the internal reservoir of the breast shield to the exterior surface of the breast shield, wherein the channel is an only opening between the internal reservoir of the breast shield and the exterior surface of the breast shield; and
a breast shield tubing extending along the channel, an end of the breast shield tubing connecting to collection tubing, wherein the breast shield tubing is configured to transmit suction to an interior portion of the breast shield such that breast milk exits the breast shield through the breast shield tubing.

* * * * *